US012758739B2

(12) United States Patent
O'Mahony et al.

(10) Patent No.: US 12,758,739 B2
(45) Date of Patent: Oct. 13, 2026

(54) SYSTEMS AND METHODS FOR REDUCING INSOMNIA-RELATED SYMPTOMS

(71) Applicant: ResMed Sensor Technologies Limited, Sandyford (IE)

(72) Inventors: Niall O'Mahony, Dublin (IE); Cesar Lopes, Dublin (IE); Michael Wren, Dublin (IE); Redmond Shouldice, Dublin (IE)

(73) Assignee: ResMed Sensor Technologies Limited, Dublin (IE)

( * ) Notice: Subject to any disclaimer, the term of this patent is extended or adjusted under 35 U.S.C. 154(b) by 996 days.

(21) Appl. No.: 17/794,363

(22) PCT Filed: Jan. 30, 2021

(86) PCT No.: PCT/IB2021/050748
§ 371 (c)(1),
(2) Date: Jul. 21, 2022

(87) PCT Pub. No.: WO2021/152549
PCT Pub. Date: Aug. 5, 2021

(65) Prior Publication Data
US 2023/0048000 A1 Feb. 16, 2023

Related U.S. Application Data

(60) Provisional application No. 62/968,725, filed on Jan. 31, 2020.

(51) Int. Cl.
*A61M 21/02* (2006.01)
*A61B 5/00* (2006.01)
(Continued)

(52) U.S. Cl.
CPC ..... *A61M 21/02* (2013.01); *A61M 2205/3303* (2013.01); *A61M 2205/502* (2013.01); *A61M 2205/52* (2013.01)

(58) Field of Classification Search
CPC .......... A61M 21/02; A61M 2205/3303; A61M 2205/502; A61M 2205/52;
(Continued)

(56) References Cited

U.S. PATENT DOCUMENTS

2012/0238800 A1* 9/2012 Naujokat .............. A61B 5/1118 600/26
2014/0008373 A1 1/2014 Sharp et al.
2016/0151603 A1* 6/2016 Shouldice .............. G16H 20/70 600/26

FOREIGN PATENT DOCUMENTS

WO 2008096307 A1 8/2008
WO 2012/012835 A2 2/2012
(Continued)

OTHER PUBLICATIONS

International Search Report in International Patent Application No. PCT/IB2021/050748 mailed May 3, 2021 (3 pp.).
(Continued)

*Primary Examiner* — Carrie R Dorna
*Assistant Examiner* — Joshua Daryl D Lannu
(74) *Attorney, Agent, or Firm* — NIXON PEABODY LLP

(57) ABSTRACT

A system includes a memory storing a user profile for a user of the system and machine-readable instructions and a control system including one or more processors configured to execute the machine-readable instructions to receive physiological data associated with the user during a sleep session, determine, based at least in part on the received physiological data, a set of sleep-related parameters for the sleep session, subsequent to the sleep session, select one of the set of sleep-related parameters as a targeted parameter, the selection of the targeted parameter being based at least in part on the stored user profile, the set of sleep-related parameters, or both, and cause information to be communicated to the user via a user device, the information being
(Continued)

indicative of the targeted parameter, a recommendation associated with improving the targeted parameter for the user in one or more subsequent sleep sessions, or both.

24 Claims, 7 Drawing Sheets

(51) Int. Cl.

| | |
|---|---|
| ***A61B 5/0205*** | (2006.01) |
| ***A61B 5/024*** | (2006.01) |
| ***A61B 5/08*** | (2006.01) |
| ***A61B 5/1455*** | (2006.01) |
| ***A61M 16/00*** | (2006.01) |
| ***A61M 16/06*** | (2006.01) |
| ***A61M 16/16*** | (2006.01) |
| ***G16H 10/20*** | (2018.01) |
| ***G16H 20/30*** | (2018.01) |
| ***G16H 20/70*** | (2018.01) |
| ***G16H 50/20*** | (2018.01) |
| ***G16H 50/30*** | (2018.01) |

(58) Field of Classification Search

CPC .............. A61M 16/0066; A61M 16/06; A61M 16/1005; A61M 16/16; A61M 16/161; A61M 2016/0027; A61M 2016/0039; A61M 2205/3306; A61M 2205/332; A61M 2205/3331; A61M 2205/3368; A61M 2205/3375; A61M 2205/505; A61M 2230/04; A61M 2230/10; A61M 2230/205; A61M 2230/60; A61M 2230/63; A61M 16/024; A61B 5/0022; A61B 5/6819; A61B 5/682; A61B 5/02405; A61B 5/02416; A61B 5/0077; A61B 5/02055; A61B 5/0816; A61B 5/14551; A61B 5/318; A61B 5/369; A61B 5/389; A61B 5/4812; A61B 2562/0204; A61B 5/4815; G16H 10/20; G16H 20/30; G16H 20/70; G16H 50/20; G16H 50/30

See application file for complete search history.

(56) References Cited

FOREIGN PATENT DOCUMENTS

| | | | |
|---|---|---|---|
| WO | 2014/047310 | A1 | 3/2014 |
| WO | 2015/006364 | A2 | 1/2015 |
| WO | 2016/061629 | A1 | 4/2016 |
| WO | 2017/032873 | A2 | 3/2017 |
| WO | 2017/132726 | A1 | 8/2017 |
| WO | 2018/050913 | A1 | 3/2018 |
| WO | 2019/122413 | A1 | 6/2019 |
| WO | 2019/122414 | A1 | 6/2019 |
| WO | 2020/104465 | A2 | 5/2020 |
| WO | 2021152549 | A1 | 8/2021 |

OTHER PUBLICATIONS

Written Opinion in International Patent Application No. PCT/IB2021/050748 mailed May 3, 2021 (8 pp.).

* cited by examiner

SYSTEMS AND METHODS FOR REDUCING INSOMNIA-RELATED SYMPTOMS

CROSS-REFERENCE TO RELATED APPLICATIONS

This application is a U.S. National Stage of International Application No. PCT/IB2021/050748, filed Jan. 30, 2021, which claims the benefit of, and priority to, U.S. Provisional Patent Application No. 62/968,725, filed Jan. 31, 2020, each of which is hereby incorporated by reference herein in its entirety.

TECHNICAL FIELD

The present disclosure relates generally to systems and methods for monitoring insomnia and reducing insomnia-related symptoms, and more particularly, to systems and methods for identifying a target sleep-related parameter and communicating information indicative of the target sleep-related parameter to the user to promote sleep.

BACKGROUND

Many individuals suffer from insomnia (e.g., difficulty initiating sleep, frequent or prolonged awakenings after initially falling asleep, and an early awakening with an inability to return to sleep) or other sleep and/or respiratory-related disorders (e.g., periodic limb movement disorder (PLMD), Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), etc.). Many of these sleep related disorders can be treated or managed by causing the user to modify their behavior, activities, and/or environmental parameters (e.g., bed time, activity level, diet, etc.). Thus, it would be advantageous to identify a targeted sleep-related parameter that is predicted to impact one or more insomnia-related symptoms and communicate information to the user to aid in reducing the one or more insomnia-related symptoms. The present disclosure is directed to solving these and other problems.

SUMMARY

According to some implementations of the present disclosure, a system includes an electronic interface, a memory, and a control system. The electronic interface is configured to receive (i) first physiological data associated with a user during a first sleep session, the first physiological data being generated by a first sensor, (ii) second data associated with the user subsequent to the first sleep session and prior to a second sleep session, and (iii) third physiological data associated with the user during the second sleep session. The memory stores machine-readable instructions. The control system includes one or more processors configured to execute the machine-readable instructions to determine a first set of sleep-related parameters for the first sleep session based at least in part on the first physiological data. The control system is further configured to identify a first one of the first set of sleep-related parameters as a first targeted parameter based at least in part on a user profile associated with the user. The control system is further configured to cause first information indicative of (i) the first targeted parameter, (ii) a first recommendation associated with the first targeted parameter, or both (i) and (ii) to be communicated to the user via a user device. The control system is further configured to update the user profile to include at least a portion of the determined first set of sleep-related parameters and at least a portion of the second data. The control system is further configured to determine a second set of sleep-related parameters for the second sleep session based at least in part on the third physiological data. The control system is further configured to identify a second one of the second set of sleep-related parameters as a second targeted parameter based at least in part on the updated user profile. The control system is further configured to cause second information indicative of (i) the second targeted parameter, (ii) a second recommendation associated with the second targeted parameter, or both (i) and (ii) to be communicated to the user via the user device.

According to some implementations of the present disclosure, a method includes receiving first physiological data associated with a user during a first sleep session. The method also includes determining a first set of sleep-related parameters for the first sleep session based at least in part on the first physiological data. The method also includes identifying a first one of the first set of sleep-related parameters as a first targeted parameter based at least in part on a user profile associated with the user. The method also includes causing first information indicative of the first targeted parameter to be communicated to the user. The method also includes receiving second data associated with the user subsequent to the first sleep session and prior to a second sleep session, wherein the second data includes user feedback, physiological data, environmental data, or any combination thereof. The method also includes updating the user profile to include at least a portion of the determined first set of sleep-related parameters and at least a portion of the second data. The method also includes receiving third physiological data associated with the user during the second sleep session. The method also includes identifying a second one of the second set of sleep-related parameters as a second targeted parameter based at least in part on the updated user profile. The method also includes causing second information indicative of the second targeted parameter to be communicated to the user.

According to some implementations of the present disclosure, a system includes a memory and a control system. The memory stores a user profile for a user of the system and machine-readable instructions. The control system includes one or more processors configured to execute the machine-readable instructions to receive physiological data associated with the user during a sleep session. The control system is further configured to determine, based at least in part on the received physiological data, a set of sleep-related parameters for the sleep session. The control system is further configured to, subsequent to the sleep session, select one of the set of sleep-related parameters as a targeted parameter, the selection of the targeted parameter being based at least in part on the stored user profile, the set of sleep-related parameters, or both. The control system is further configured to cause information to be communicated to the user via a user device, the information being indicative of (i) the targeted parameter, (ii) a recommendation associated with improving the targeted parameter for the user in one or more subsequent sleep sessions, or both (i) and (ii).

According to some implementations of the present disclosure, a system includes a memory and a control system. The memory stores a user profile for a user of the system and machine-readable instructions. The control system includes one or more processors configured to execute the machine-readable instructions to receive physiological data associated with the user during a sleep session. The control system is further configured to determine, based at least in part on the received physiological data, a set of sleep-related parameters for the sleep session. The control system is further configured to, subsequent to the sleep session, select one of the set of sleep-related parameters as a targeted parameter, the selection of the targeted parameter being based at least in part on the stored user profile, the set of sleep-related parameters, or both. The control system is further configured to cause information to be communicated to the user via a user device, the information being indicative of (i) a recommendation associated with improving the targeted parameter for the user in one or more subsequent sleep sessions and (ii) a second one of the set of sleep-related parameters that is different from the targeted parameter, or a score associated with second one of the set of sleep-related parameters.

According to some implementations of the present disclosure, a system includes an electronic interface, a memory, and a control system. The electronic interface is configured to receive (i) first physiological data associated with a user during a first sleep session and (ii) second physiological data associated with the user during a second sleep session, the first physiological data and the second physiological data being generated by one or more sensors. The memory stores machine-readable instructions. The control system includes one or more processors configured to execute the machine-readable instructions to determine a first set of sleep-related parameters, wherein the first set of sleep-related parameters is determined for the first sleep session based at least in part on the first physiological data. The control system is further configured to determine a first plurality of insomnia-related scores, wherein the first plurality of insomnia-related scores is determined for the first sleep session, each one of the first plurality of insomnia-related scores being associated with a corresponding one of the first set of sleep-related parameters. The control system is further configured to determine that a first one of the first plurality of insomnia-related scores satisfies a first predetermined condition. The control system is further configured to cause a first indication to be communicated to the user via a user device, the first indication being of (i) the first one of the first plurality of insomnia-related scores, (ii) the first one of the first set of sleep-related parameters, or (iii) both (i) and (ii). The control system is further configured to determine a second set of sleep-related parameters, wherein the second set of sleep-related parameters is determined for the second sleep session based at least in part on the second physiological data. The control system is further configured to determine a second plurality of insomnia-related scores, wherein the second plurality of insomnia-related scores is determined for the second sleep session, each one of the second plurality of insomnia-related scores being associated with a corresponding one of the second set of sleep-related parameters. The control system is further configured to determine that a second one of the second plurality of insomnia-related scores satisfies a second predetermined condition. The control system is further configured to cause a second indication to be communicated to the user via the user device, the second indication being of (i) the second one of the second plurality of insomnia-related scores, (ii) the second one of the second set of sleep-related parameter, or (iii) both (i) and (ii).

According to some implementations of the present disclosure, a method includes receiving first physiological data associated with a user for a first sleep session. The method also includes determining a first set of sleep-related parameters based at least in part on the first physiological data. The method also includes determining a first plurality of insomnia-related scores for the first sleep session, each one of the first plurality of insomnia-related scores being associated with a corresponding one of the first set of sleep-related parameters. The method also includes identifying a first one of the first plurality of insomnia-related scores that satisfies a first predetermined condition. The method also includes causing a first indication to be communicated to the user via a user device, the first indication being of (i) the first one of the first plurality of insomnia-related scores, (ii) the first one of the first set of sleep-related parameters, or (iii) both (i) and (ii). The method also includes receiving second physiological data associated with a user for a second sleep session, wherein the second sleep session is subsequent to the first sleep session. The method also includes determining a second set of sleep-related parameters, wherein the second set of sleep-related parameters is determined for the second sleep session based at least in part on the second physiological data. The method also includes determining a second plurality of insomnia-related scores, wherein the second plurality of insomnia-related scores is determined for the second sleep session, each one of the second plurality of insomnia-related scores being associated with a corresponding one of the second set of sleep-related parameters. The method also includes identifying a second one of the second plurality of insomnia-related scores that satisfies a second predetermined condition. The method also includes causing a second indication to be communicated to the user via the user device, the second indication being of (i) the second one of the second plurality of insomnia-related scores, (ii) the second one of the second set of sleep-related parameters, or (iii) both (i) and (ii).

According to some implementations of the present disclosure, a system includes an electronic interface, a memory, and a control system. The electronic interface is configured to receive (i) first physiological data associated with a user during a first sleep session and (ii) second physiological data associated with the user during a second sleep session, the first physiological data and the second physiological data being generated by one or more sensors. The memory stores machine-readable instructions. The control system includes one or more processors configured to execute the machine-readable instructions to determine a first insomnia-related score and a second insomnia-related score for the first sleep session based at least in part on the first physiological data, the first insomnia-related score being associated with a first sleep-related parameter, the second insomnia-related score being associated with a second sleep-related parameter. The control system is further configured to determine that the first insomnia-related score is greater than the second sleep-related score. The control system is further configured to cause a first indication of the first insomnia-related score to be communicated to the user via a user device. The control system is further configured to determine a third insomnia-related score and a fourth insomnia-related score for the second sleep session based at least in part on the second physiological data, the third insomnia-related score being associated with the first sleep-related parameter, the fourth insomnia-related score being associated with the second sleep-related parameter.

The above summary is not intended to represent each implementation or every aspect of the present disclosure. Additional features and benefits of the present disclosure are apparent from the detailed description and figures set forth below.

Figure 1:
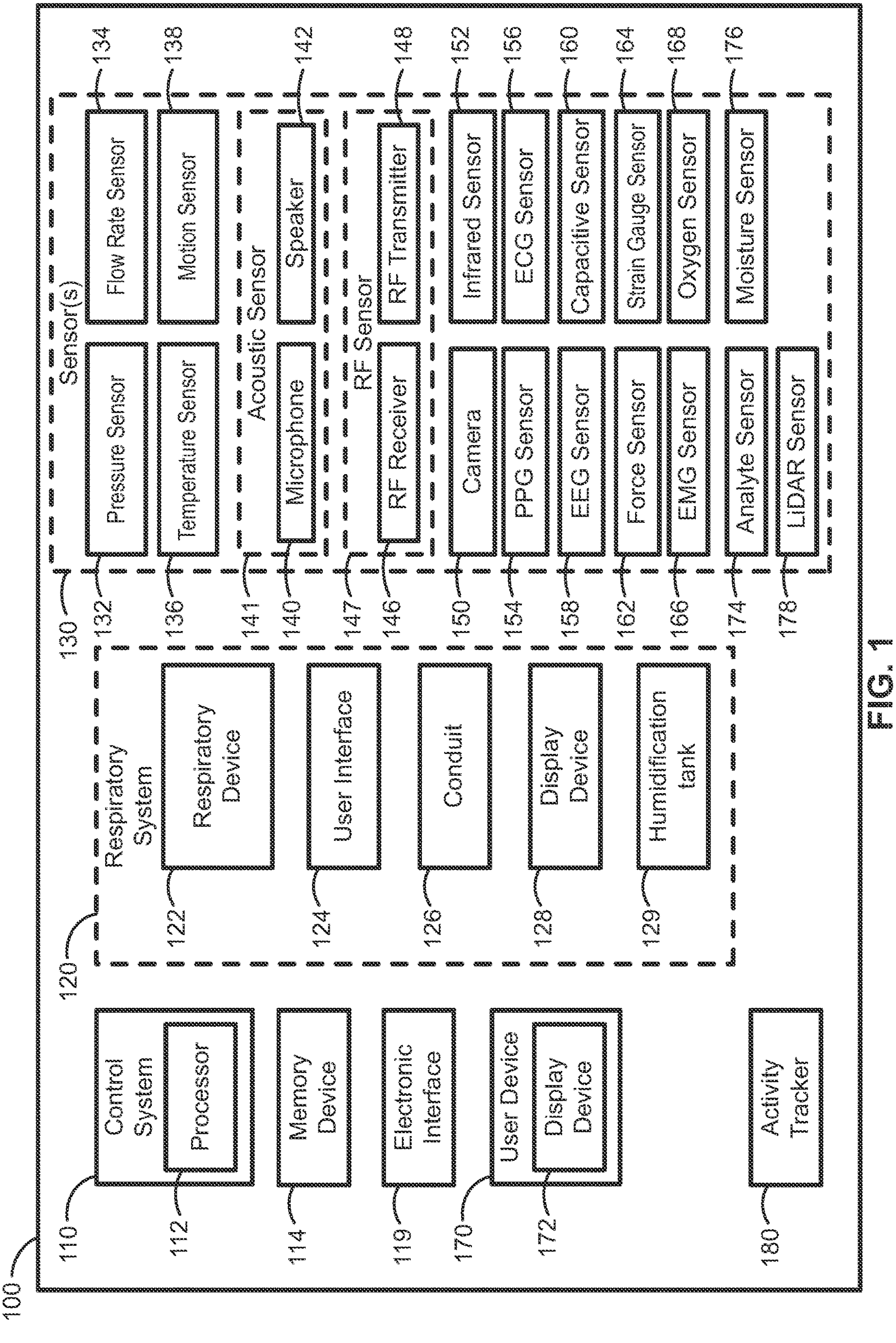
FIG. 1 is a functional block diagram of a system for determining one or more sleep-related parameters for a sleep session, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

Many individuals suffer from insomnia, a condition which is generally characterized by a dissatisfaction with sleep quality or duration (e.g., difficulty initiating sleep, frequent or prolonged awakenings after initially falling asleep, and an early awakening with an inability to return to sleep). It is estimated that over 2.6 billion people worldwide experience some form of insomnia, and over 750 million people worldwide suffer from a diagnosed insomnia disorder. In the United States, insomnia causes an estimated gross economic burden of $107.5 billion per year, and accounts for 13.6% of all days out of role and 4.6% of injuries requiring medical attention. Recent research also shows that insomnia is the second most prevalent mental disorder, and that insomnia is a primary risk factor for depression.

Nocturnal insomnia symptoms generally include, for example, reduced sleep quality, reduced sleep duration, sleep-onset insomnia, sleep-maintenance insomnia, late insomnia, mixed insomnia, and/or paradoxical insomnia. Sleep-onset insomnia is characterized by difficulty initiating sleep at bedtime. Sleep-maintenance insomnia is characterized by frequent and/or prolonged awakenings during the night after initially falling asleep. Late insomnia is characterized by an early morning awakening (e.g., prior to a target or desired wakeup time) with the inability to go back to sleep. Comorbid insomnia refers to a type of insomnia where the insomnia symptoms are caused at least in part by a symptom or complication of another physical or mental condition (e.g., anxiety, depression, medical conditions, and/or medication usage). Mixed insomnia refers to a combination of attributes of other types of insomnia (e.g., a combination of sleep-onset, sleep-maintenance, and late insomnia symptoms). Paradoxical insomnia refers to a disconnect or disparity between the user's perceived sleep quality and the user's actual sleep quality.

Diurnal (e.g., daytime) insomnia symptoms include, for example, fatigue, reduced energy, impaired cognition (e.g., attention, concentration, and/or memory), difficulty functioning in academic or occupational settings, and/or mood disturbances. These symptoms can lead to psychological complications such as, for example, lower performance, decreased reaction time, increased risk of depression, and/or increased risk of anxiety disorders. Insomnia symptoms can also lead to physiological complications such as, for example, poor immune system function, high blood pressure, increased risk of heart disease, increased risk of diabetes, weight gain, and/or obesity.

Insomnia can also be categorized based on its duration. For example, insomnia symptoms are typically considered acute or transient if they occur for less than 3 months. Conversely, insomnia symptoms are typically considered chronic or persistent if they occur for 3 months or more, for example. Persistent/chronic insomnia symptoms often require a different treatment path than acute/transient insomnia symptoms.

Mechanisms of insomnia include predisposing factors, precipitating factors, and perpetuating factors. Predisposing factors include hyperarousal, which is characterized by increased physiological arousal during sleep and wakefulness. Measures of hyperarousal include, for example, increased levels of cortisol, increased activity of the autonomic nervous system (e.g., as indicated by increase resting heart rate and/or altered heart rate), increased brain activity (e.g., increased EEG frequencies during sleep and/or increased number of arousals during REM sleep), increased metabolic rate, increased body temperature and/or increased activity in the pituitary-adrenal axis. Precipitating factors include stressful life events (e.g., related to employment or education, relationships, etc.) Perpetuating factors include excessive worrying about sleep loss and the resulting consequences, which may maintain insomnia symptoms even after the precipitating factor has been removed.

Once diagnosed, insomnia can be managed or treated using a variety of techniques or providing recommendations to the patient. Generally, the patient can be encouraged or recommended to generally practice healthy sleep habits (e.g., plenty of exercise and daytime activity, have a routine, no bed during the day, eat dinner early, relax before bedtime, avoid caffeine in the afternoon, avoid alcohol, make bedroom comfortable, remove bedroom distractions, get out of bed if not sleepy, try to wake up at the same time each day regardless of bed time) or discouraged from certain habits (e.g., do not work in bed, do not go to bed too early, do not go to bed if not tired). An individual suffering from insomnia can be treated by improving the sleep hygiene of the individual. Sleep hygiene generally refers to the individual's practices (e.g., die, exercise, substance use, bedtime, activities before going to sleep, activities in bed before going to sleep, etc.) and/or environmental parameters (e.g., ambient light, ambient noise, ambient temperature, etc.). In at least some cases, the individual can improve their sleep hygiene by going to bed at a certain bedtime each night, sleeping for a certain duration, waking up at a certain time, modifying the environmental parameters, or any combination thereof.

Examples of sleep-related and/or respiratory disorders include Periodic Limb Movement Disorder (PLMD), Restless Leg Syndrome (RLS), Sleep-Disordered Breathing (SDB), Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), and chest wall disorders. Obstructive Sleep Apnea (OSA), a form of Sleep Disordered Breathing (SDB), is characterized by events including occlusion or obstruction of the upper air passage during sleep resulting from a combination of an abnormally small upper airway and the normal loss of muscle tone in the region of the tongue, soft palate and posterior oropharyngeal wall. Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterized by repetitive de-oxygenation and re-oxygenation of the arterial blood. Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness. Chronic Obstructive Pulmonary Disease (COPD) encompasses any of a group of lower airway diseases that have certain characteristics in common, such as increased resistance to air movement, extended expiratory phase of respiration, and loss of the normal elasticity of the lung. Neuromuscular Disease (NMD) encompasses many diseases and ailments that impair the functioning of the muscles either directly via intrinsic muscle pathology, or indirectly via nerve pathology. Chest wall disorders are a group of thoracic deformities that result in inefficient coupling between the respiratory muscles and the thoracic cage.

These other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that occur when the individual is sleeping. While these other sleep-related disorders may have similar symptoms as insomnia, distinguishing these other sleep-related disorders from insomnia is useful for tailoring an effective treatment plan distinguishing characteristics that may call for different treatments. For example, fatigue is generally a feature of insomnia, whereas excessive daytime sleepiness is a characteristic feature of other disorders (e.g., PLMD) and reflects a physiological propensity to fall asleep unintentionally.

Referring to FIG. 1, a system 100, according to some implementations of the present disclosure, is illustrated. The system 100 includes a control system 110, a memory device 114, an electronic interface 119, one or more sensors 130, and one or more user devices 170. In some implementation, the system 100 further optionally includes a respiratory therapy system 120 and an activity tracker.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is illustrated in FIG. 1, the control system 110 can include any number of processors (e.g., one processor, two processors, five processors, ten processors, etc.) that can be in a single housing, or located remotely from each other. The control system 110 (or any other control system) or a portion of the control system 110 such as the processor 112 (or any other processor(s) or portion(s) of any other control system), can be used to carry out one or more steps of any of the methods described and/or claimed herein. The control system 110 can be coupled to and/or positioned within, for example, a housing of the external device 170, and/or within a housing of one or more of the sensors 130. The control system 110 can be centralized (within one such housing) or decentralized (within two or more of such housings, which are physically distinct). In such implementations including two or more housings containing the control system 110, such housings can be located proximately and/or remotely from each other.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within a housing of a respiratory therapy device 122 of the respiratory therapy system 120, within a housing of the user device 170, within a housing of one or more of the sensors 130, or any combination thereof. Like the control system 110, the memory device 114 can be centralized (within one such housing) or decentralized (within two or more of such housings, which are physically distinct).

In some implementations, the memory device 114 (FIG. 1) stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a family history of insomnia or sleep apnea, an employment status of the user, an educational status of the user, a socioeconomic status of the user, or any combination thereof. The medical information can include, for example, information indicative of one or more medical conditions associated with the user, medication usage by the user, or both. The medical information data can further include a multiple sleep latency test (MSLT) result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

The electronic interface 119 is configured to receive data (e.g., physiological data and/or audio data) from the one or more sensors 130 such that the data can be stored in the memory device 114 and/or analyzed by the processor 112 of the control system 110. The electronic interface 119 can communicate with the one or more sensors 130 using a wired connection or a wireless connection (e.g., using an RF communication protocol, a WiFi communication protocol, a Bluetooth communication protocol, over a cellular network, etc.). The electronic interface 119 can include an antenna, a receiver (e.g., an RF receiver), a transmitter (e.g., an RF transmitter), a transceiver, or any combination thereof. The electronic interface 119 can also include one more processors and/or one more memory devices that are the same as, or similar to, the processor 112 and the memory device 114 described herein. In some implementations, the electronic interface 119 is coupled to or integrated in the user device 170. In other implementations, the electronic interface 119 is coupled to or integrated (e.g., in a housing) with the control system 110 and/or the memory device 114.

As noted above, in some implementations, the system 100 optionally includes a respiratory system 120. The respiratory system 120 can include a respiratory pressure therapy device 122 (referred to herein as respiratory device 122), a user interface 124, a conduit 126 (also referred to as a tube or an air circuit), a display device 128, a humidification tank 129, or any combination thereof. In some implementations, the control system 110, the memory device 114, the display device 128, one or more of the sensors 130, and the humidification tank 129 are part of the respiratory device 122. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory system 120 is generally used to treat individuals suffering from one or more sleep-related respiratory disorders (e.g., obstructive sleep apnea, central sleep apnea, or mixed sleep apnea).

The respiratory device 122 is generally used to generate pressurized air that is delivered to a user (e.g., using one or more motors that drive one or more compressors). In some implementations, the respiratory device 122 generates continuous constant air pressure that is delivered to the user. In other implementations, the respiratory device 122 generates two or more predetermined pressures (e.g., a first predetermined air pressure and a second predetermined air pressure). In still other implementations, the respiratory device 122 is configured to generate a variety of different air pressures within a predetermined range. For example, the respiratory device 122 can deliver at least about 6 cm $H_2O$, at least about 10 cm $H_2O$, at least about 20 cm $H_2O$, between about 6 cm $H_2O$ and about 10 cm $H_2O$, between about 7 cm $H_2O$ and about 12 cm $H_2O$, etc. The respiratory device 122 can also deliver pressurized air at a predetermined flow rate between, for example, about −20 L/min and about 150 L/min, while maintaining a positive pressure (relative to the ambient pressure).

The user interface 124 engages a portion of the user's face and delivers pressurized air from the respiratory device 122 to the user's airway to aid in preventing the airway from narrowing and/or collapsing during sleep. This may also increase the user's oxygen intake during sleep. Depending upon the therapy to be applied, the user interface 124 may form a seal, for example, with a region or portion of the user's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 cm$H_2O$.

Figure 2:
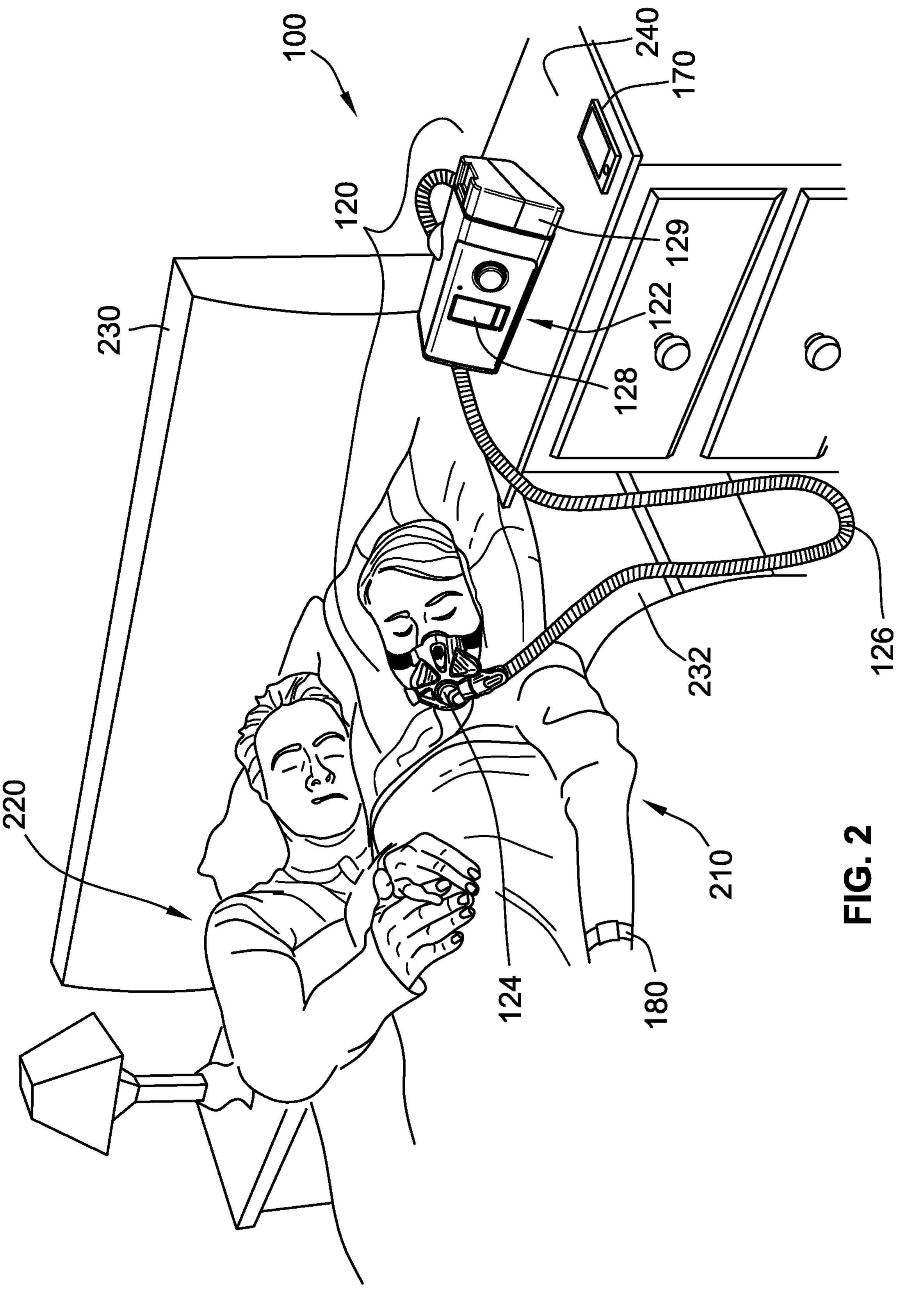
FIG. 2 is a perspective view of at least a portion of the system of FIG. 1, a user, and a bed partner, according to some implementations of the present disclosure.

As shown in FIG. 2, in some implementations, the user interface 124 is a facial mask that covers the nose and mouth of the user. Alternatively, the user interface 124 can be a nasal mask that provides air to the nose of the user or a nasal pillow mask that delivers air directly to the nostrils of the user. The user interface 124 can include a plurality of straps (e.g., including hook and loop fasteners) for positioning and/or stabilizing the interface on a portion of the user (e.g., the face) and a conformal cushion (e.g., silicone, plastic, foam, etc.) that aids in providing an air-tight seal between the user interface 124 and the user. The user interface 124 can also include one or more vents for permitting the escape of carbon dioxide and other gases exhaled by the user 210. In other implementations, the user interface 124 includes a mouthpiece (e.g., a night guard mouthpiece molded to conform to the user's teeth, a mandibular repositioning device, etc.).

The conduit 126 (also referred to as an air circuit or tube) allows the flow of air between two components of a respiratory system 120, such as the respiratory device 122 and the user interface 124. In some implementations, there can be separate limbs of the conduit for inhalation and exhalation. In other implementations, a single limb conduit is used for both inhalation and exhalation.

One or more of the respiratory device 122, the user interface 124, the conduit 126, the display device 128, and the humidification tank 129 can contain one or more sensors (e.g., a pressure sensor, a flow rate sensor, or more generally any of the other sensors 130 described herein). These one or more sensors can be use, for example, to measure the air pressure and/or flow rate of pressurized air supplied by the respiratory device 122.

The display device 128 is generally used to display image(s) including still images, video images, or both and/or information regarding the respiratory device 122. For example, the display device 128 can provide information regarding the status of the respiratory device 122 (e.g., whether the respiratory device 122 is on/off, the pressure of the air being delivered by the respiratory device 122, the temperature of the air being delivered by the respiratory device 122, etc.) and/or other information (e.g., a sleep score and/or a therapy score (also referred to as a myAir™ score, such as described in WO 2016/061629, which is hereby incorporated by reference herein in its entirety), the current date/time, personal information for the user 210, etc.). In some implementations, the display device 128 acts as a human-machine interface (HMI) that includes a graphic user interface (GUI) configured to display the image(s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory device 122.

The humidification tank 129 is coupled to or integrated in the respiratory device 122 and includes a reservoir of water that can be used to humidify the pressurized air delivered from the respiratory device 122. The respiratory device 122 can include a heater to heat the water in the humidification tank 129 in order to humidify the pressurized air provided to the user. Additionally, in some implementations, the conduit 126 can also include a heating element (e.g., coupled to and/or imbedded in the conduit 126) that heats the pressurized air delivered to the user.

The respiratory system 120 can be used, for example, as a positive airway pressure (PAP) system, a continuous positive airway pressure (CPAP) system, an automatic positive airway pressure system (APAP), a bi-level or variable positive airway pressure system (BPAP or VPAP), a ventilator, or any combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Referring to FIG. 2, a portion of the system 100 (FIG. 1), according to some implementations, is illustrated. A user 210 of the respiratory system 120 and a bed partner 220 are located in a bed 230 and are laying on a mattress 232. The user interface 124 (e.g., a full facial mask) can be worn by the user 210 during a sleep session. The user interface 124 is fluidly coupled and/or connected to the respiratory device 122 via the conduit 126. In turn, the respiratory device 122 delivers pressurized air to the user 210 via the conduit 126 and the user interface 124 to increase the air pressure in the throat of the user 210 to aid in preventing the airway from closing and/or narrowing during sleep. The respiratory device 122 can be positioned on a nightstand 240 that is directly adjacent to the bed 230 as shown in FIG. 2, or more generally, on any surface or structure that is generally adjacent to the bed 230 and/or the user 210.

Referring to back to FIG. 1, the one or more sensors 130 of the system 100 include a pressure sensor 132, a flow rate sensor 134, temperature sensor 136, a motion sensor 138, a microphone 140, a speaker 142, a radio-frequency (RF) receiver 146, a RF transmitter 148, a camera 150, an infrared sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, or any combination thereof. Generally, each of the one or sensors 130 are configured to output sensor data that is received and stored in the memory device 114 or one or more other memory devices.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the infrared sensor 152, the photoplethysmogram (PPG) sensor 154, the electrocardiogram (ECG) sensor 156, the electroencephalography (EEG) sensor 158, the capacitive sensor 160, the force sensor 162, the strain gauge sensor 164, the electromyography (EMG) sensor 166, the oxygen sensor 168, the analyte sensor 174, the moisture sensor 176 more generally, the one or more sensors 130 can include any combination and any number of each of the sensors described and/or shown herein.

The physiological data generated by one or more of the sensors 130 can be used by the control system 110 to determine a sleep-wake signal associated with a user during a sleep session and one or more sleep-related parameters. The sleep-wake signal can be indicative of one or more sleep states, including wakefulness, relaxed wakefulness, micro-awakenings, or distinct sleep stages such as a rapid eye movement (REM) stage, a first non-REM stage (often referred to as "N1"), a second non-REM stage (often referred to as "N2"), a third non-REM stage (often referred to as "N3"), or any combination thereof. Methods for determining sleep states and/or sleep stages from physiological data generated by one or more of the sensors, such as sensors 130, are described in, for example, WO 2014/047310, US 2014/0088373, WO 2017/132726, WO 2019/122413, and WO 2019/122414, each of which is hereby incorporated by reference herein in its entirety.

The sleep-wake signal can also be timestamped to determine a time that the user enters the bed, a time that the user exits the bed, a time that the user attempts to fall asleep, etc. The sleep-wake signal can be measured by the sensor(s) 130 during the sleep session at a predetermined sampling rate, such as, for example, one sample per second, one sample per 30 seconds, one sample per minute, etc. In some implementations, the sleep-wake signal can also be indicative of a respiration signal, a respiration rate, an inspiration amplitude, an expiration amplitude, an inspiration-expiration ratio, a number of events per hour, a pattern of events, pressure settings of the respiratory device 122, or any combination thereof during the sleep session. The event(s) can include snoring, apneas, central apneas, obstructive apneas, mixed apneas, hypopneas, a mask leak (e.g., from the user interface 124), a restless leg, a sleeping disorder, choking, an increased heart rate, labored breathing, an asthma attack, an epileptic episode, a seizure, or any combination thereof. The one or more sleep-related parameters that can be determined for the user during the sleep session based on the sleep-wake signal include, for example, a total time in bed, a total sleep time, a sleep onset latency, a wake-after-sleep-onset parameter, a sleep efficiency, a fragmentation index, or any combination thereof. As described in further detail herein, the physiological data and/or the sleep-related parameters can be analyzed to determine one or more insomnia-related scores.

The pressure sensor 132 outputs pressure data that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory system 120 and/or ambient pressure. In such implementations, the pressure sensor 132 can be coupled to or integrated in the respiratory device 122. The pressure sensor 132 can be, for example, a capacitive sensor, an electromagnetic sensor, a piezoelectric sensor, a strain-gauge sensor, an optical sensor, a potentiometric sensor, or any combination thereof.

The flow rate sensor 134 outputs flow rate data that can be stored in the memory device 114 and/or analyzed by the processor 112 of the control system 110. Examples of flow rate sensors (such as, for example, the flow rate sensor 134) are described in International Publication No. WO 2012/012835, which is hereby incorporated by reference herein in its entirety. In some implementations, the flow rate sensor 134 is used to determine an air flow rate from the respiratory device 122, an air flow rate through the conduit 126, an air flow rate through the user interface 124, or any combination thereof. In such implementations, the flow rate sensor 134 can be coupled to or integrated in the respiratory device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof. In some implementations, the flow rate data can be analyzed to determine cardiogenic oscillations of the user.

The temperature sensor 136 outputs temperature data that can be stored in the memory device 114 and/or analyzed by the processor 112 of the control system 110. In some implementations, the temperature sensor 136 generates temperatures data indicative of a core body temperature of the user 210 (FIG. 2), a skin temperature of the user 210, a temperature of the air flowing from the respiratory device 122 and/or through the conduit 126, a temperature in the user interface 124, an ambient temperature, or any combination thereof. The temperature sensor 136 can be, for example, a thermocouple sensor, a thermistor sensor, a silicon band gap temperature sensor or semiconductor-based sensor, a resistance temperature detector, or any combination thereof.

The microphone 140 outputs sound data that can be stored in the memory device 114 and/or analyzed by the processor 112 of the control system 110. The microphone 140 can be used to record sound(s) during a sleep session (e.g., sounds from the user 210) to determine (e.g., using the control system 110) one or more sleep-related parameters, as described in further detail herein. The microphone 140 can be coupled to or integrated in the respiratory device 122, the use interface 124, the conduit 126, or the user device 170.

The speaker 142 outputs sound waves that are audible to a user of the system 100 (e.g., the user 210 of FIG. 2). The speaker 142 can be used, for example, as an alarm clock or to play an alert or message to the user 210 (e.g., in response to an event). The speaker 142 can be coupled to or integrated in the respiratory device 122, the user interface 124, the conduit 126, or the external device 170.

The microphone 140 and the speaker 142 can be used as separate devices. In some implementations, the microphone 140 and the speaker 142 can be combined into an acoustic sensor 141, as described in, for example, WO 2018/050913 and WO 2020/104465, each of which is hereby incorporated by reference herein in its entirety. In such implementations, the speaker 142 generates or emits sound waves at a predetermined interval and the microphone 140 detects the reflections of the emitted sound waves from the speaker 142. The sound waves generated or emitted by the speaker 142 have a frequency that is not audible to the human ear (e.g., below 20 Hz or above around 18 kHz) so as not to disturb the sleep of the user 210 or the bed partner 220 (FIG. 2). Based at least in part on the data from the microphone 140 and/or the speaker 142, the control system 110 can determine a location of the user 210 (FIG. 2) and/or one or more of the sleep-related parameters described in herein such as, for example, a respiration signal, a respiration rate, an inspiration amplitude, an expiration amplitude, an inspiration-expiration ratio, a number of events per hour, a pattern of events, a sleep state, a sleep stage, pressure settings of the respiratory device 122, or any combination thereof. In this context, a sonar sensor may be understood to concern an active acoustic sensing, such as by generating/transmitting ultrasound or low frequency ultrasound sensing signals (e.g., in a frequency range of about 17-23 kHz, 18-22 kHz, or 17-18 kHz, for example), through the air. Such a system may be considered in relation to WO2018/050913 and WO 2020/104465 mentioned above.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location of the user 210 (FIG. 2) and/or one or more of the sleep-related parameters described herein. An RF receiver (either the RF receiver 146 and the RF transmitter 148 or another RF pair) can also be used for wireless communication between the control system 110, the respiratory device 122, the one or more sensors 130, the user device 170, or any combination thereof. While the RF receiver 146 and RF transmitter 148 are shown as being separate and distinct elements in FIG. 1, in some implementations, the RF receiver 146 and RF transmitter 148 are combined as a part of an RF sensor 147. In some such implementations, the RF sensor 147 includes a control circuit. The specific format of the RF communication could be WiFi, Bluetooth, etc.

In some implementations, the RF sensor 147 is a part of a mesh system. One example of a mesh system is a WiFi mesh system, which can include mesh nodes, mesh router(s), and mesh gateway(s), each of which can be mobile/movable or fixed. In such implementations, the WiFi mesh system includes a WiFi router and/or a WiFi controller and one or more satellites (e.g., access points), each of which include an RF sensor that the is the same as, or similar to, the RF sensor 147. The WiFi router and satellites continuously communicate with one another using WiFi signals. The WiFi mesh system can be used to generate motion data based on changes in the WiFi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 150 outputs image data reproducible as one or more images (e.g., still images, video images, thermal images, or a combination thereof) that can be stored in the memory device 114. The image data from the camera 150 can be used by the control system 110 to determine one or more of the sleep-related parameters described herein. For example, the image data from the camera 150 can be used to identify a location of the user, to determine a time when the user 210 enters the bed 230 (FIG. 2), and to determine a time when the user 210 exits the bed 230.

The infrared (IR) sensor 152 outputs infrared image data reproducible as one or more infrared images (e.g., still images, video images, or both) that can be stored in the memory device 114. The infrared data from the IR sensor 152 can be used to determine one or more sleep-related parameters during a sleep session, including a temperature of the user 210 and/or movement of the user 210. The IR sensor 152 can also be used in conjunction with the camera 150 when measuring the presence, location, and/or movement of the user 210. The IR sensor 152 can detect infrared light having a wavelength between about 700 nm and about 1 mm, for example, while the camera 150 can detect visible light having a wavelength between about 380 nm and about 740 nm.

The PPG sensor 154 outputs physiological data associated with the user 210 (FIG. 2) that can be used to determine one or more sleep-related parameters, such as, for example, a heart rate, a heart rate variability, a cardiac cycle, respiration rate, an inspiration amplitude, an expiration amplitude, an inspiration-expiration ratio, estimated blood pressure parameter(s), or any combination thereof. The PPG sensor 154 can be worn by the user 210, embedded in clothing and/or fabric that is worn by the user 210, embedded in and/or coupled to the user interface 124 and/or its associated headgear (e.g., straps, etc.), etc.

The ECG sensor 156 outputs physiological data associated with electrical activity of the heart of the user 210. In some implementations, the ECG sensor 156 includes one or more electrodes that are positioned on or around a portion of the user 210 during the sleep session. The physiological data from the ECG sensor 156 can be used, for example, to determine one or more of the sleep-related parameters described herein.

The EEG sensor 158 outputs physiological data associated with electrical activity of the brain of the user 210. In some implementations, the EEG sensor 158 includes one or more electrodes that are positioned on or around the scalp of the user 210 during the sleep session. The physiological data from the EEG sensor 158 can be used, for example, to determine a sleep state or sleep stage of the user 210 at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, or any combination thereof. In some implementations, the one or more sensors 130 also include a galvanic skin response (GSR) sensor, a blood flow sensor, a respiration sensor, a pulse sensor, a sphygmomanometer sensor, an oximetry sensor, or any combination thereof.

The analyte sensor 174 can be used to detect the presence of an analyte in the exhaled breath of the user 210. The data output by the analyte sensor 174 can be stored in the memory device 114 and used by the control system 110 to determine the identity and concentration of any analytes in the breath of the user 210. In some implementations, the analyte sensor 174 is positioned near a mouth of the user 210 to detect analytes in breath exhaled from the user 210's mouth. For example, when the user interface 124 is a facial mask that covers the nose and mouth of the user 210, the analyte sensor 174 can be positioned within the facial mask to monitor the user 210's mouth breathing. In other implementations, such as when the user interface 124 is a nasal mask or a nasal pillow mask, the analyte sensor 174 can be positioned near the nose of the user 210 to detect analytes in breath exhaled through the user's nose. In still other implementations, the analyte sensor 174 can be positioned near the user 210's mouth when the user interface 124 is a nasal mask or a nasal pillow mask. In this implementation, the analyte sensor 174 can be used to detect whether any air is inadvertently leaking from the user 210's mouth. In some implementations, the analyte sensor 174 is a volatile organic compound (VOC) sensor that can be used to detect carbon-based chemicals or compounds. In some implementations, the analyte sensor 174 can also be used to detect whether the user 210 is breathing through their nose or mouth. For example, if the data output by an analyte sensor 174 positioned near the mouth of the user 210 or within the facial mask (in implementations where the user interface 124 is a facial mask) detects the presence of an analyte, the control system 110 can use this data as an indication that the user 210 is breathing through their mouth.

The moisture sensor 176 outputs data that can be stored in the memory device 114 and used by the control system 110. The moisture sensor 176 can be used to detect moisture in various areas surrounding the user (e.g., inside the conduit 126 or the user interface 124, near the user 210's face, near the connection between the conduit 126 and the user interface 124, near the connection between the conduit 126 and the respiratory device 122, etc.). Thus, in some implementations, the moisture sensor 176 can be coupled to or integrated in the user interface 124 or in the conduit 126 to monitor the humidity of the pressurized air from the respiratory device 122. In other implementations, the moisture sensor 176 is placed near any area where moisture levels need to be monitored. The moisture sensor 176 can also be used to monitor the humidity of the ambient environment surrounding the user 210, for example, the air inside the bedroom.

While shown separately in FIG. 1, any combination of the one or more sensors 130 can be integrated in and/or coupled to any one or more of the components of the system 100, including the respiratory device 122, the user interface 124, the conduit 126, the humidification tank 129, the control system 110, the user device 170, or any combination thereof. For example, the acoustic sensor 141 and/or the RF sensor 147 can be integrated in and/or coupled to the user device 170. In such implementations, the user device 170 can be considered a secondary device that generates additional or secondary data for use by the system 100 (e.g., the control system 110) according to some aspects of the present disclosure. In some implementations, at least one of the one or more sensors 130 is not coupled to the respiratory device 122, the control system 110, or the user device 170, and is positioned generally adjacent to the user 210 during the sleep session (e.g., positioned on or in contact with a portion of the user 210, worn by the user 210, coupled to or positioned on the nightstand, coupled to the mattress, coupled to the ceiling, etc.).

The user device 170 (FIG. 1) includes a display device 172. The user device 170 can be, for example, a mobile device such as a smart phone, a tablet, a laptop, or the like. Alternatively, the user device 170 can be an external sensing system, a television (e.g., a smart television) or another smart home device (e.g., a smart speaker(s) such as Google Home, Amazon Echo, Alexa etc.). In some implementations, the user device is a wearable device (e.g., a smart watch). The display device 172 is generally used to display image(s) including still images, video images, or both. In some implementations, the display device 172 acts as a human-machine interface (HMI) that includes a graphic user interface (GUI) configured to display the image(s) and an input interface. The display device 172 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 170. In some implementations, one or more user devices can be used by and/or included in the system 100.

While the control system 110 and the memory device 114 are described and shown in FIG. 1 as being a separate and distinct component of the system 100, in some implementations, the control system 110 and/or the memory device 114 are integrated in the user device 170 and/or the respiratory device 122. Alternatively, in some implementations, the control system 110 or a portion thereof (e.g., the processor 112) can be located in a cloud (e.g., integrated in a server, integrated in an Internet of Things (IoT) device, connected to the cloud, be subject to edge cloud processing, etc.), located in one or more servers (e.g., remote servers, local servers, etc., or any combination thereof.

While system 100 is shown as including all of the components described above, more or fewer components can be included in a system for generating physiological data and determining a recommended notification or action for the user according to implementations of the present disclosure. For example, a first alternative system includes the control system 110, the memory device 114, and at least one of the one or more sensors 130. As another example, a second alternative system includes the control system 110, the memory device 114, at least one of the one or more sensors 130, and the user device 170. As yet another example, a third alternative system includes the control system 110, the memory device 114, the respiratory system 120, at least one of the one or more sensors 130, and the user device 170. Thus, various systems can be formed using any portion or portions of the components shown and described herein and/or in combination with one or more other components.

Figure 3:
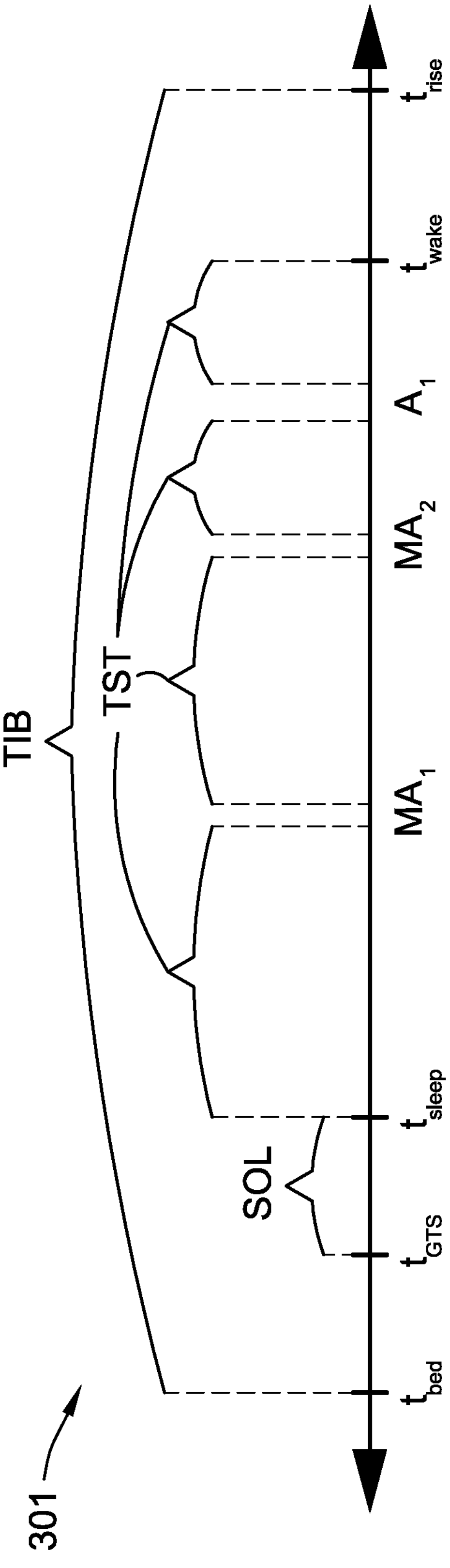
FIG. 3 illustrates an exemplary timeline for a sleep session, according to some implementations of the present disclosure.

As used herein, a sleep session can be defined in a number of ways based on, for example, an initial start time and an end time. Referring to FIG. 3, an exemplary timeline 300 for a sleep session is illustrated. The timeline 300 includes an enter bed time ($t_{bed}$), a go-to-sleep time ($t_{GTS}$), an initial sleep time ($t_{sleep}$), a first micro-awakening $MA_1$ and a second micro-awakening $MA_2$, a wake-up time ($t_{wake}$), and a rising time ($t_{rise}$).

As used herein, a sleep session can be defined in multiple ways. For example, a sleep session can be defined by an initial start time and an end time. In some implementations, a sleep session is a duration where the user is asleep, that is, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smart phone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

Referring to FIG. 3, an exemplary timeline 300 for a sleep session is illustrated. The timeline 300 includes an enter bed time ($t_{bed}$), a go-to-sleep time ($t_{GTS}$), an initial sleep time ($t_{sleep}$), a first micro-awakening $MA_1$, a second micro-awakening $MA_2$, an awakening A, a wake-up time ($t_{wake}$), and a rising time ($t_{rise}$).

The enter bed time $t_{bed}$ is associated with the time that the user initially enters the bed (e.g., bed 230 in FIG. 2) prior to falling asleep (e.g., when the user lies down or sits in the bed). The enter bed time $t_{bed}$ can be identified based on a bed threshold duration to distinguish between times when the user enters the bed for sleep and when the user enters the bed for other reasons (e.g., to watch TV). For example, the bed threshold duration can be at least about 10 minutes, at least about 20 minutes, at least about 30 minutes, at least about 45 minutes, at least about 1 hour, at least about 2 hours, etc. While the enter bed time $t_{bed}$ is described herein in reference to a bed, more generally, the enter time $t_{bed}$ can refer to the time the user initially enters any location for sleeping (e.g., a couch, a chair, a sleeping bag, etc.).

The go-to-sleep time (GTS) is associated with the time that the user initially attempts to fall asleep after entering the bed ($t_{bed}$). For example, after entering the bed, the user may engage in one or more activities to wind down prior to trying to sleep (e.g., reading, watching TV, listening to music, using the user device 170, etc.). The initial sleep time ($t_{sleep}$) is the time that the user initially falls asleep. For example, the initial sleep time ($t_{sleep}$) can be the time that the user initially enters the first non-REM sleep stage.

The wake-up time $t_{wake}$ is the time associated with the time when the user wakes up without going back to sleep (e.g., as opposed to the user waking up in the middle of the night and going back to sleep). The user may experience one of more unconscious microawakenings (e.g., microawakenings $MA_1$ and $MA_2$) having a short duration (e.g., 5 seconds, 10 seconds, 30 seconds, 1 minute, etc.) after initially falling asleep. In contrast to the wake-up time $t_{wake}$, the user goes back to sleep after each of the microawakenings $MA_1$ and $MA_2$. Similarly, the user may have one or more conscious awakenings (e.g., awakening A) after initially falling asleep (e.g., getting up to go to the bathroom, attending to children or pets, sleep walking, etc.). However, the user goes back to sleep after the awakening A. Thus, the wake-up time $t_{wake}$ can be defined, for example, based on a wake threshold duration (e.g., the user is awake for at least 15 minutes, at least 20 minutes, at least 30 minutes, at least 1 hour, etc.).

Similarly, the rising time $t_{rise}$ is associated with the time when the user exits the bed and stays out of the bed with the intent to end the sleep session (e.g., as opposed to the user getting up during the night to go to the bathroom, to attend to children or pets, sleep walking, etc.). In other words, the rising time $t_{rise}$ is the time when the user last leaves the bed without returning to the bed until a next sleep session (e.g., the following evening). Thus, the rising time $t_{rise}$ can be defined, for example, based on a rise threshold duration (e.g., the user has left the bed for at least 15 minutes, at least 20 minutes, at least 30 minutes, at least 1 hour, etc.). The enter bed time $t_{bed}$ time for a second, subsequent sleep session can also be defined based on a rise threshold duration (e.g., the user has left the bed for at least 4 hours, at least 6 hours, at least 8 hours, at least 12 hours, etc.).

As described above, the user may wake up and get out of bed one more times during the night between the initial $t_{bed}$ and the final $t_{rise}$. In some implementations, the final wake-up time $t_{wake}$ and/or the final rising time $t_{rise}$ that are identified or determined based on a predetermined threshold duration of time subsequent to an event (e.g., falling asleep or leaving the bed). Such a threshold duration can be customized for the user. For a standard user which goes to bed in the evening, then wakes up and goes out of bed in the morning any period (between the user waking up ($t_{wake}$) or raising up ($t_{rise}$), and the user either going to bed ($t_{bed}$), going to sleep ($t_{GTS}$) or falling asleep ($t_{sleep}$) of between about 12 and about 18 hours can be used. For users that spend longer periods of time in bed, shorter threshold periods may be used (e.g., between about 8 hours and about 14 hours). The threshold period may be initially selected and/or later adjusted based on the system monitoring the user's sleep behavior.

The total time in bed (TIB) is the duration of time between the time enter bed time $t_{bed}$ and the rising time $t_{rise}$. The total sleep time (TST) is associated with the duration between the initial sleep time and the wake-up time, excluding any conscious or unconscious awakenings and/or micro-awakenings therebetween. Generally, the total sleep time (TST) will be shorter than the total time in bed (TIB) (e.g., one minute short, ten minutes shorter, one hour shorter, etc.). For example, referring to the timeline 300 of FIG. 3, the total sleep time (TST) spans between the initial sleep time $t_{sleep}$ and the wake-up time $t_{wake}$, but excludes the duration of the first micro-awakening $MA_1$, the second micro-awakening $MA_2$, and the awakening A. As shown, in this example, the total sleep time (TST) is shorter than the total time in bed (TIB).

In some implementations, the total sleep time (TST) can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., about 30 seconds), then back into the wakefulness stage for a short period (e.g., one minute), and then goes back to the first non-REM stage. In this example, the persistent total sleep time excludes the first instance (e.g., about 30 seconds) of the first non-REM stage.

In some implementations, the sleep session is defined as starting at the enter bed time ($t_{bed}$) and ending at the rising time ($t_{rise}$), i.e., the sleep session is defined as the total time in bed (TIB). In some implementations, a sleep session is defined as starting at the initial sleep time ($t_{sleep}$) and ending at the wake-up time ($t_{wake}$). In some implementations, the sleep session is defined as the total sleep time (TST). In some implementations, a sleep session is defined as starting at the go-to-sleep time ($t_{GTS}$) and ending at the wake-up time ($t_{wake}$). In some implementations, a sleep session is defined as starting at the go-to-sleep time ($t_{GTS}$) and ending at the rising time ($t_{rise}$). In some implementations, a sleep session is defined as starting at the enter bed time ($t_{bed}$) and ending at the wake-up time ($t_{wake}$). In some implementations, a sleep session is defined as starting at the initial sleep time ($t_{sleep}$) and ending at the rising time ($t_{rise}$).

Figure 4:
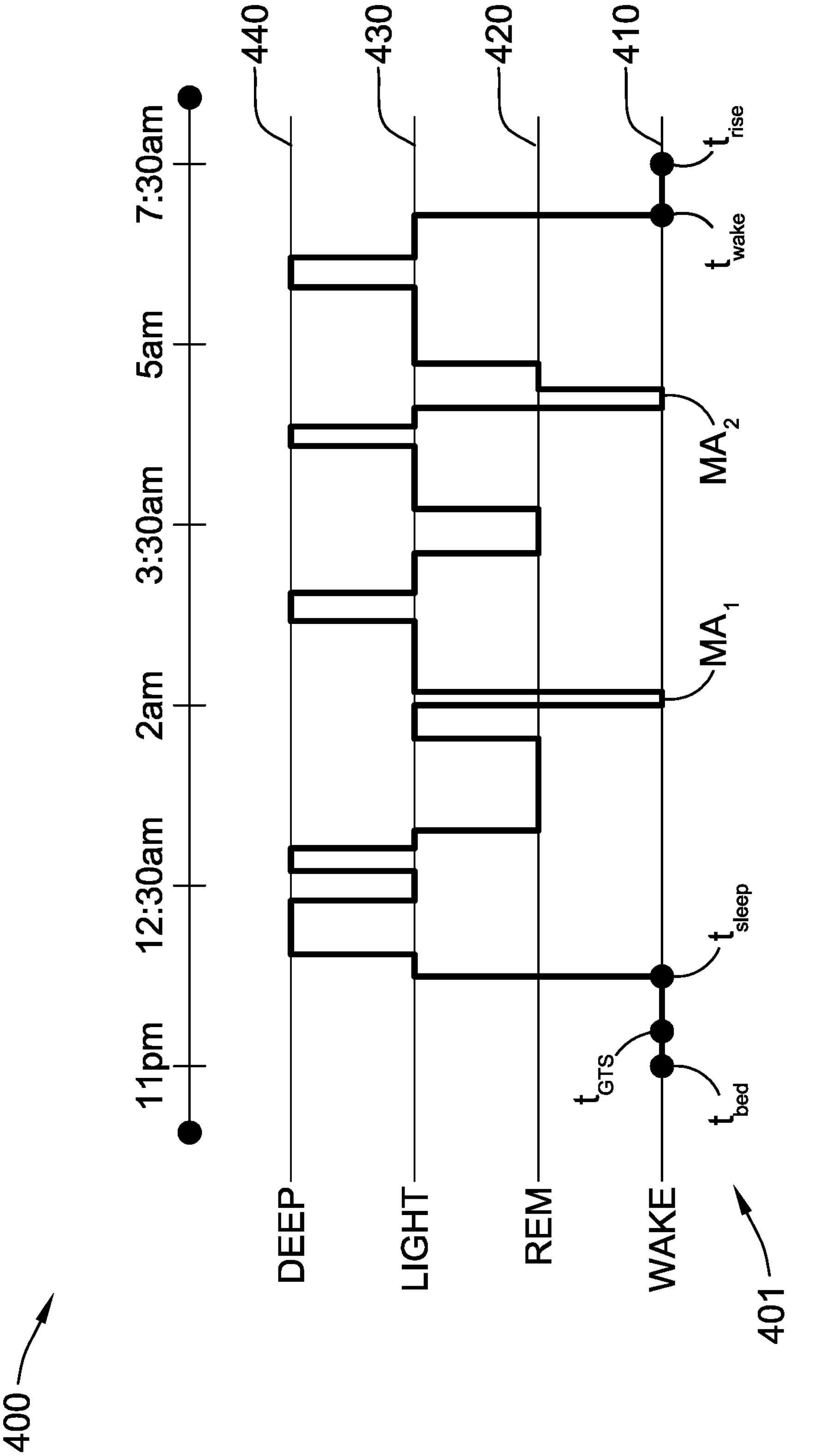
FIG. 4 illustrates an exemplary hypnogram associated with the sleep session of FIG. 3, according to some implementations of the present disclosure.

Referring to FIG. 4, an exemplary hypnogram 400 corresponding to the timeline 300 (FIG. 3), according to some implementations, is illustrated. As shown, the hypnogram 400 includes a sleep-wake signal 401, a wakefulness stage axis 410, a REM stage axis 420, a light sleep stage axis 430, and a deep sleep stage axis 440. The intersection between the sleep-wake signal 401 and one of the axes 410-440 is indicative of the sleep stage at any given time during the sleep session.

The sleep-wake signal 401 can be generated based on physiological data associated with the user (e.g., generated by one or more of the sensors 130 described herein). The sleep-wake signal can be indicative of one or more sleep states, including wakefulness, relaxed wakefulness, micro-awakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. While the hypnogram 400 is shown in FIG. 4 as including the light sleep stage axis 430 and the deep sleep stage axis 440, in some implementations, the hypnogram 400 can include an axis for each of the first non-REM stage, the second non-REM stage, and the third non-REM stage. In other implementations, the sleep-wake signal can also be indicative of a respiration signal, a respiration rate, an inspiration amplitude, an expiration amplitude, an inspiration-expiration ratio, a number of events per hour, a pattern of events, or any combination thereof. Information describing the sleep-wake signal can be stored in the memory device 114.

The hypnograph 400 can be used to determine one or more sleep-related parameters, such as, for example, a sleep onset latency (SOL), wake-after-sleep onset (WASO), a sleep efficiency (SE), a sleep fragmentation index, sleep blocks, or any combination thereof.

The sleep onset latency (SOL) is defined as the time between the go-to-sleep time ($t_{GTS}$) and the initial sleep time ($t_{sleep}$). In other words, the sleep onset latency is indicative of the time that it took the user to actually fall asleep after initially attempting to fall asleep. In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement therebetween. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings $MA_1$ and $MA_2$ shown in FIG. 4), whether conscious or unconscious. In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized). In some implementations, the sleep efficiency (SE) can be calculated based on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening $MA_1$ and micro-awakening $MA_2$ shown in FIG. 4), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, 30 seconds.

In some implementations, the systems and methods described herein can include generating or analyzing a hypnogram including a sleep-wake signal to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof based at least in part on the sleep-wake signal of a hypnogram.

In other implementations, one or more of the sensors 130 can be used to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof, which in turn define the sleep session. For example, the enter bed time $t_{bed}$ can be determined based on, for example, data generated by the motion sensor 138, the microphone 140, the camera 150, or any combination thereof. The go-to-sleep time can be determined based on, for example, data from the motion sensor 138 (e.g., data indicative of no movement by the user), data from the camera 150 (e.g., data indicative of no movement by the user and/or that the user has turned off the lights) data from the microphone 140 (e.g., data indicative of the using turning off a TV), data from the user device 170 (e.g., data indicative of the user no longer using the user device 170), data from the pressure sensor 132 and/or the flow rate sensor 134 (e.g., data indicative of the user turning on the respiratory device 122, data indicative of the user donning the user interface 124, etc.), or any combination thereof.

Figure 5A:
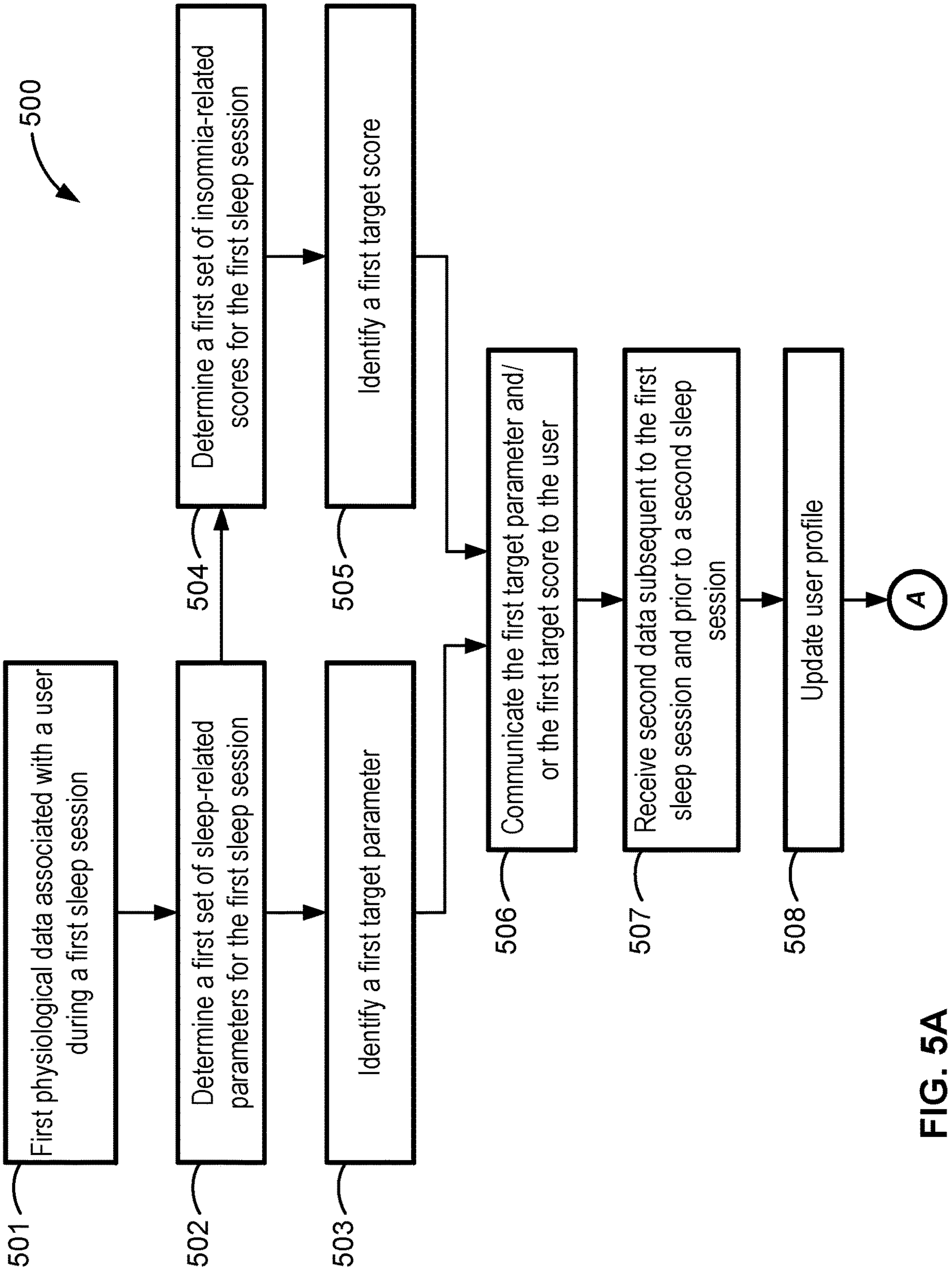
FIG. 5A is a process flow diagram for a first portion of a method of determining one or more targeted sleep-related parameters, according to some implementations of the present disclosure.
Figure 5B:
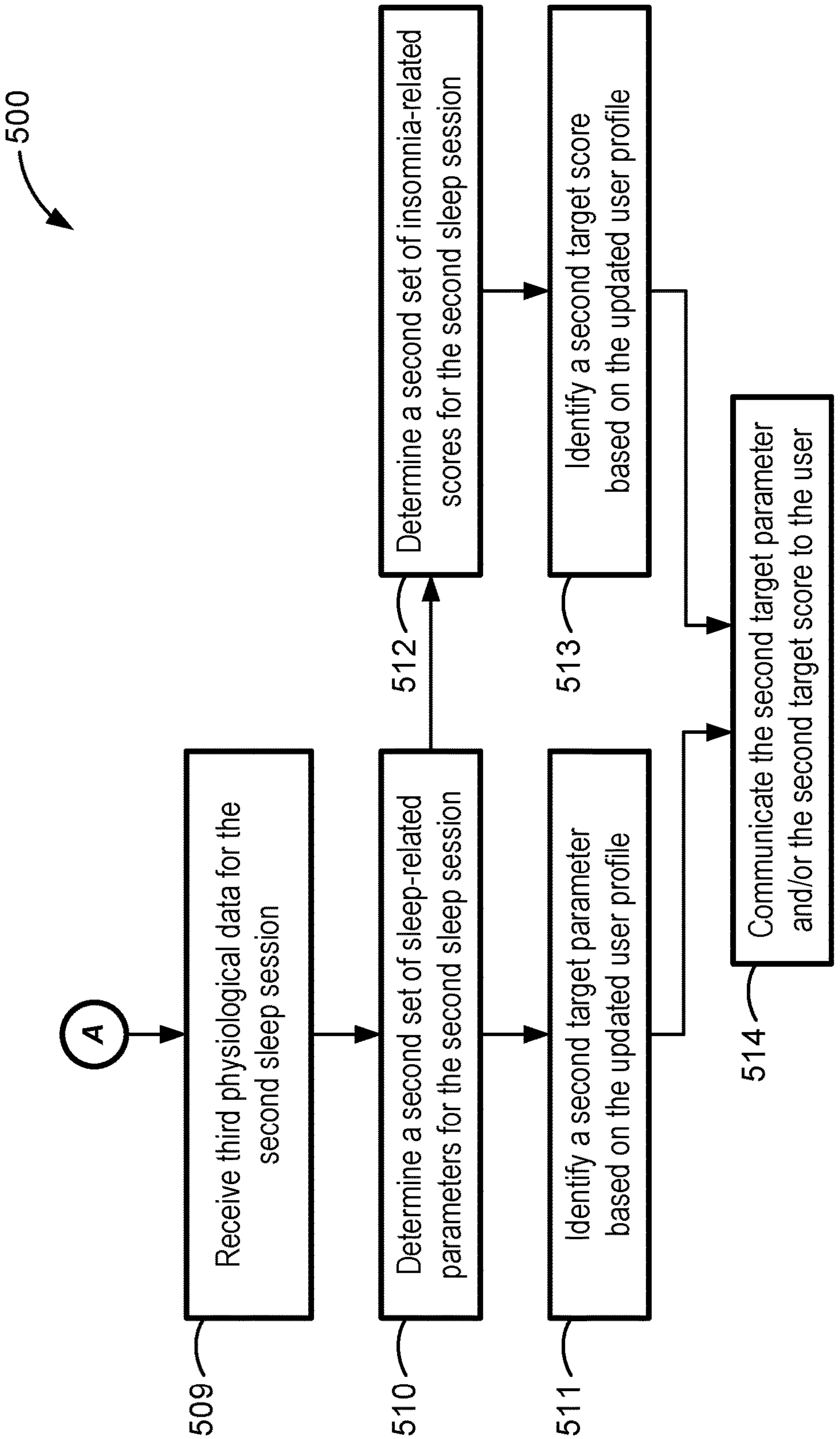
FIG. 5B is a process flow diagram for a second portion of the method of determining one or more targeted sleep-related parameters of FIG. 5A, according to some implementations of the present disclosure.

Referring to FIG. 5, a method 500 for determining one or more target sleep-related parameters and/or insomnia-related scores is illustrated. One or more steps of the method 500 can be implemented using any element or aspect of the system 100 (FIGS. 1-2) described herein.

Step 501 of the method 500 includes generating and receiving first physiological data associated with a user during at least a portion of a first sleep session. The first physiological data can be received by, for example, the electronic interface 119 (FIG. 1) described herein. The first physiological data can be generated or obtained by at least one of the one or more sensors 130 (FIG. 1). For example, in some implementations, the first physiological data is generated using the acoustic sensor 141 or the RF sensor 147 described above, which are coupled to or integrated in the user device 170. In other implementations, the first physiological data is generated or obtained using the pressure sensor 132 and/or the flow rate sensor 134 (FIG. 1), which are coupled to or integrated in the respiratory device 122. Information describing the first physiological data generated during step 501 can be stored in the memory device 114 (FIG. 1).

Step 501 can include generating first physiological data during a segment of the first sleep session, during the entirety of the first sleep session, or across multiple segments of the first sleep session. For example, step 501 can include generating the first physiological data continuously or discontinuously during between about 1% and 100% of the first sleep session, at least 10% of the first sleep session, at least 30% of the first sleep session, at least 50% of the first sleep session, at least 90% of the first sleep session, etc.

Step 502 of the method 500 includes determining a first set of sleep-related parameters for the first sleep session based at least in part on the first physiological data generated during step 501. For example, the control system 110 can analyze the first physiological data (e.g., that is stored in the memory device 114) to determine the first set of sleep-related parameters for the first sleep session. The first set of sleep-related parameters can include, for example, a sleep onset latency for the first sleep session, a total light sleep time for the first sleep session, a total deep sleep time for the first sleep session, a total REM sleep time for the first sleep session, a total sleep time for the first sleep session, a number of awakenings during the first sleep session, a frequency of awakenings during the first sleep session, a respiration signal during at least a portion of the first sleep session, a respiration rate during at least a portion of the first sleep session, an inspiration amplitude during at least a portion of the first sleep session, an expiration amplitude during at least a portion of the first sleep session, an inspiration-expiration ratio during at least a portion of the first sleep session, one or more events during at least a portion of the first sleep session, a number of events per hour during at least a portion of the first sleep session, a pattern of events during at least a portion of the first sleep session, a sleep state during at least a portion of the first sleep session, or any combination thereof. The one or more events can include snoring, apneas, central apneas, obstructive apneas, mixed apneas, hypopneas, a mask leak, a cough, a restless leg, a sleeping disorder, choking, a heart rate, labored breathing, an asthma attack, an epileptic episode, a seizure, increased blood pressure, or any combination thereof. Information describing the first set of sleep-related parameters for the first sleep session generated during step 502 can be stored in the memory device 114 (FIG. 1), for example.

In some implementations of the method 500, the memory device 114 (FIG. 1) stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a family history of insomnia, an employment status of the user, an educational status of the user, a socioeconomic status of the user, or any combination thereof. The medical information can include, for example, including indicative of one or more medical conditions associated with the user, medication usage by the user, or both. The medical information data can further include a multiple sleep latency test (MSLT) test result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

Step 503 of the method 500 includes identifying a first one of the first set of sleep-related parameters (step 502) that is a first target parameter. Generally, the target parameter is a sleep-related parameter that is to be communicated to the user subsequent to the first sleep session (as described in more detail in connection with step 506) to aid in reducing or preventing insomnia-related symptoms for a second sleep session that is subsequent to the first sleep session (e.g., the next successive sleep session after the first sleep session). The target parameter is generally identified as the one of the first set of sleep-related parameters that is predicted to influence the behavior of the user and improve the quality of sleep (e.g., reduce insomnia-related symptoms) for the second sleep session. That is, the target parameter is identified as being the parameter that will be most effective in improving the quality of sleep if communicated to the user prior to the next sleep session (e.g., along with one or more recommendations for improving the target parameter).

For example, step 503 can include using the control system 110 can analyze the first physiological data and/or compare the first physiological data with the user profile stored in the memory device 114 to identify or determine the first target parameter. In some implementations, step 503 can include using an algorithm to identify the target parameter. In such implementations, the algorithm can be trained using data from the user profile data (e.g., previously recorded data associated with the user) and/or other data sources (e.g., data associated with other individuals besides the user) to identify the target parameter. The algorithm can be, for example, a machine learning algorithm, (e.g., supervised or unsupervised) or a neural network (e.g., shallow or deep approaches).

In some implementations, the method 500 optionally includes step 504. Step 504 includes determining a first set of insomnia-related sleep scores for the first sleep session based at least in part on the first set of sleep-related parameters (step 502). Each of the first set of insomnia-related sleep scores determining during step 504 is associated with one or more of the first set of sleep-related parameters determined during step 502. The insomnia-related scores determined by scaling or standardizing the associated sleep-related parameter based on previously recorded sleep-related parameters for the user, previously recorded sleep-related parameters for a plurality of other users, or any combination thereof that are stored in the user profile. An insomnia-related sleep score can be, for example, a numerical value that is on a predetermined scale (e.g., between 1-10, between 1-100, etc.), a letter grade (e.g., A, B, C, D, or F), or a descriptor (e.g., poor, fair, good, excellent, average, below average, needs improvement, etc.). In some implementations, the insomnia-related score can be a sleep score, such as the ones described in International Publication No. WO 2015/006364, which is hereby incorporated by reference herein in its entirety.

For an illustrative example in the case of an insomnia-related score that is associated with the total sleep time parameter, the insomnia-related score can be determined by comparing the total sleep time parameter (e.g., 6 hours) with previously recorded total sleep time parameters include in the associated user profile. For example, if the average of the previously recorded total sleep time parameters is 8 hours, this value can be scaled to a value of 10 on a scale of 1-10, such that if the total sleep time parameter is 6 hours, the insomnia-related score would be 7.5 for that sleep session. Alternatively, the insomnia-related score can be determined by scaling the associated with parameter with a desired or target value for the parameter (e.g., a desired or target total sleep time).

In implementations of the method 500 including step 504, the method 500 can also optionally include step 505. Step 505 includes identifying a first one of the first set of insomnia-related scores that is a first target score. The first target score can be identified or selected in the same or similar manner as described above for the first target parameter during step 503. That is, generally, the first target score is one of the first set of insomnia-related scores that is to be improved for the user during a second sleep session that is subsequent to the first sleep session (e.g., the next successive sleep session after the first sleep session).

Step 506 of the method 500 includes communicating, to the user, information indicative of the determined first target parameter (step 503), information indicative of the first target score (step 505), or both. In some implementations, step 506 includes communicating the information to the user via the display device 172 of the user device 170 described herein. In other implementations, step 506 of the method 500 additionally or alternatively includes causing an audio indication to be communicated to the user (e.g., via the speaker 142).

In some implementations, step 506 also includes communicating a first recommendation to the user subsequent to the first sleep session. The first recommendation can be determined based at least in part using information in the associated user profile (e.g., using the same or similar algorithms as used to determine the target parameter). Generally, the recommendation can encourage the user to generally practice healthy sleep habits (e.g., plenty of exercise and daytime activity, have a routine, no bed during the day, eat dinner early, relax before bedtime, avoid caffeine in the afternoon, avoid alcohol, make bedroom comfortable, remove bedroom distractions, get out of bed if not sleepy, try to wake up at the same time each day regardless of bed time) or discouraged from certain habits (e.g., do not work in bed, do not go to bed too early, do not go to bed if not tired) to improve the determined target parameter and/or target score. An individual suffering from insomnia can be treated by improving the sleep hygiene of the individual, including a bedtime, activities before going to sleep, activities in bed before going to sleep and/or environmental parameters (e.g., ambient light, ambient noise, ambient temperature, etc.). In at least some cases, the individual can improve their sleep hygiene by going to bed at a certain bedtime each night, sleeping for a certain duration, waking up at a certain time, modifying the environmental parameters, or any combination thereof.

In one example, the first recommendation can include a recommended bedtime for the second sleep session. The recommended bedtime for the second sleep session can be determined, for example, by determining the bedtime for which the user will have the highest predicted sleep score for the second sleep session. Such sleep scores are exemplified by the ones described in International Publication No. WO 2015/006364, which is hereby incorporated by reference herein in its entirety. Alternative definitions are also possible. The recommended bedtime can also be determined using any of the algorithms described herein.

Generally, step 506 includes automatically communicating the information described above to the user at a predetermined time that is subsequent to the first sleep session but prior to the second sleep session (e.g., between about 1 minute and about 10 hours after the first sleep session, between about 15 minutes and about 2 hours after the first sleep session, etc.). Alternatively, step 506 can include automatically communicating the information described above to the user at a predetermined time that is prior to the second sleep session but subsequent to the first sleep session (e.g., between about 1 minute and about 3 hours before the second sleep session, between about 5 minutes and about 1 hour before the second sleep session, etc.).

Step 507 of the method 500 includes receiving and/or generating second data associated with the user subsequent to the first sleep session and prior to a second sleep session. The second data can include, for example, user feedback provided by the user, physiological data, environmental data, or any combination thereof. The second data can be stored in the memory device 114 (FIG. 1).

The user feedback included in the second data generated and/or received in step 507 can include, for example, an indication of user diet, user stress, an indication of user anxiety, an indication of user inhibitors, an indication of user television usage, an indication of user caffeine usage, an indication of user drug usage, an indication of user alcohol usage, an indication of user nicotine usage, an indication of user marijuana usage, an indication of user mediations, an indication of user mental illnesses, an indication of user perceived sleep quality, an indication of user perceived sleep time, an indication of physical activity of the user, an indication of user subjective sleepiness, an indication of user subjective fatigue, or any combination thereof. Information associated with or indicative of the feedback from the user can be received, for example, through the user device 170 (e.g., via alphanumeric text, speech-to-text, etc.). In some implementations, the method 500 includes prompting the user to provide the feedback for step 507. For example, the control system 110 can cause one or more prompts to be displayed on the display device 172 of the user device 170 (FIG. 1) that provides an interface for the user to provide the feedback (e.g., the user clicks or taps to enter feedback, the user enters feedback using an alphanumeric keyboard, etc.). The received user feedback can be stored, for example, in the memory device 114 (FIG. 1) described herein.

The user-reported feedback can include, for example, a subjective sleep score for the first sleep session (e.g., poor, average, good, excellent, etc.), a subjective fatigue level (e.g., tired, average, rested), a subjective stress level (e.g., low, average, high), a subjective health status (e.g., healthy, unhealthy, sick, etc.), or any combination thereof, following the first sleep session. More generally, the user feedback can include any of the types of information described herein that are stored in the user profile (e.g., to update the user profile). The user feedback can include demographic data, such as, for example, information indicative of an age of the user, a gender of the user, a race of the user, an employment status of the user, an educational status of the user, a socioeconomic status of the user, a recent life event (e.g., change in relationship status, birth of child, death in family etc.), information as to whether the user has a family history of sleep-related disorders or any combination thereof. The user feedback can also include medical data, such as, for example, information (e.g., medical records) indicative of one or more medical conditions that the user has been diagnosed with, medication usage, or both.

The environmental parameters included in the second data generated and/or obtained ins step 507 can include, for example, ambient light, ambient noise, ambient temperature, humidity, etc.). The environmental parameters can be determined or sensed by at least one of the one or more sensors 130 (FIG. 1) described herein.

The physiological data included in the second data (hereinafter, second physiological data) generated and/or received in step 507 can be the same as, or similar to, the first physiological data (step 501) described herein, except that the second physiological data is not associated with a sleep session. For example, step 507 can include generating or obtaining second physiological data during one or more periods subsequent to the first sleep session and prior to a second sleep session using at least of the one or more sensors 130 (FIG. 1).

In such implementations of the method 500 the second data can be analyzed (e.g., by the control system 110) to determine one or more activity parameters or levels and/or to identify one or more daytime symptoms experienced by the user. As described herein, certain insomnia symptoms can be characterized as diurnal (daytime) symptoms, such as, for example, fatigue, reduced energy, impaired cognition (e.g., attention, concentration, and/or memory), difficulty functioning in academic or occupational settings, and/or mood disturbances. For example, step 509 can include determining an activity level of user during the day using the second physiological data and comparing the determined activity level to a predetermined threshold value to determine whether the user experienced symptoms of fatigue during the day. As another example, step 509 can include determining a reaction time of the user (e.g., in response to a stimulus) and comparing the determined reaction time to a predetermined threshold value to determine whether the user experienced symptoms of impaired cognition during the day.

In some implementations, the first physiological data from (step 501) is generated using a first one of the sensors 130 and the second physiological data (step 507) is generated using a second of the sensors 130 that is separate and distinct from the first sensor. In such implementations, the first sensor and the second sensor can be different types of sensors (e.g., the first sensor is an acoustic sensor that is the same as, or similar to, the acoustic sensor 141, and the second sensor is a motion sensor that is the same as, or similar to, the motion sensor 138). Alternatively, the first sensor and the second sensor can be the same sensor. As described herein, while the system 100 (FIG. 1) is shown as including one user device 170, in some implementations, the system 100 can include any number of user devices that are the same as, or similar to, the user device 170. In such implementations, a first one of the sensors 130 for generating the first physiological data (step 501) can be coupled to or integrated in a first user device (e.g., a smartphone), while a second one of the sensors 130 for generating the second physiological data (step 509) can be coupled to or integrated in a second user device (e.g., a wearable device, such as a smart watch) that is separate and distinct from the first user device.

In some implementations, the first sleep session and the second sleep session are immediately successive sleep sessions. For example, the first sleep session can begin Monday evening and end Tuesday morning, while the second sleep session begins on Tuesday evening and ends on Wednesday morning. Alternatively, there can be one or more additional, intervening sleep sessions between the first sleep session and the second sleep session such that the first sleep session and the second sleep session are not immediately successive sleep sessions. For example, the first sleep session can begin Monday evening and end Tuesday morning, an intermediate or intervening sleep session begins on Tuesday evening and ends on Wednesday morning, and the second sleep session begins on Wednesday evening and ends on Thursday morning.

The second physiological data associated can be generated ruing the entire duration between the first sleep session and the second sleep session, or during one or more segments or portion of the duration between the first sleep session and the second sleep session. For example, step 509 can include generating the second physiological data during between about 1% and about 99% of the duration between the first sleep session and the second sleep session, at least 10% of the duration between the first sleep session and the second sleep session, at least 30% of the duration between the first sleep session and the second sleep session, at least 50% of the duration between the first sleep session and the second sleep session, at least 90% of the duration between the first sleep session and the second sleep session, at least about 2 hours, at least about 5 hours, at least about 8 hours, at least about 10 hours, etc.

Step 508 of the method 500 includes updating the user profile to include at least a portion of the first physiological data (step 501), the first set of sleep-related parameters (step 502), the determined first target parameter (step 503), the first set of insomnia-related scores (step 504), the determined first target score (step 505), the second data (step 507), or any combination thereof. In some implementations, step 508 is performed once (e.g., subsequent to step 506), or one or more times (e.g., after each of steps 501-507 such that the user profile 510 is updated after each step). As described herein, updating the user profile subsequent to the first sleep session is advantageous in that the updated user profile can be used for subsequent sleep sessions (e.g., the second sleep session) to make more accurate predictions (e.g., for identifying the target parameter and/or target score).

Step 509 of the method 500 includes generating and/or receiving third physiological data associated with a user during at least a portion of the second sleep session. The third physiological data can be received by, for example, the electronic interface 119 (FIG. 1) described herein. The third physiological data can be generated or obtained by at least one of the one or more sensors 130 (FIG. 1). For example, in some implementations, the third physiological data is generated using the acoustic sensor 141 or the RF sensor 147 described above, which are coupled to or integrated in the user device 170. In other implementations, the third physiological data is generated or obtained using the pressure sensor 132 and/or the flow rate sensor 134 (FIG. 1), which are coupled to or integrated in the respiratory device 122. Information describing the third physiological data generated during step 509 can be stored in the memory device 114 (FIG. 1).

Step 509 can include generating third physiological data during a segment of the second sleep session, during the entirety of the third sleep session, or across multiple segments of the third sleep session. For example, step 509 can include generating the third physiological data continuously or discontinuously during between about 1% and 100% of the third sleep session, at least 10% of the third sleep session, at least 30% of the third sleep session, at least 50% of the third sleep session, at least 90% of the third sleep session, etc.

Step 510 of the method 500 includes determining a second set of sleep-related parameters for the second sleep session based at least in part on the third physiological data generated during step 509. For example, the control system 110 can analyze the third physiological data (e.g., that is stored in the memory device 114) to determine the second set of sleep-related parameters for the first sleep session. The second set of sleep-related parameters can be the same as, or similar to, the first set of the sleep-related parameters (step 502).

Step 511 of the method 500 includes identifying a second one of the second set of sleep-related parameters (step 510) that is a second target parameter. The second target parameter can be identified or determined in the same or similar manner as the first target parameter (step 503). The second target parameter can be the same as, or different than, the first target parameter.

In some implementations, the method 500 optionally includes step 512. Step 512 includes determining a second set of insomnia-related sleep scores for the second sleep session based at least in part on the second set of sleep-related parameters (step 510). The second set of insomnia-related sleep scores for the second sleep session can be determined in the same or similar manner as the first set of insomnia-related sleep scores (step 504).

In such implementations, the method 500 can also optionally include step 513. Step 513 includes identifying a second one of the second set of insomnia-related scores (step 512) that is a second target score. The second target score can be identified or selected in the same or similar manner as described above for the first target score (step 505).

Step 514 includes communicating, to the user, information indicative of the determined second target parameter (step 511), information indicative of the second target score (step 513), or both, in the same or similar manner as step 506 described above.

One or more of the steps of the method 500 described herein can be repeated one or more time for additional sleep sessions (e.g., a third sleep session, a fourth sleep session, a tenth sleep session, etc.). Thus, the user profile can be continuously updated over an extended period of time (e.g., weeks, months, years) to improve the identification of the target parameter and/or target score, thereby further aiding in reducing and/or preventing insomnia symptoms experienced by the user.

Figure 6:
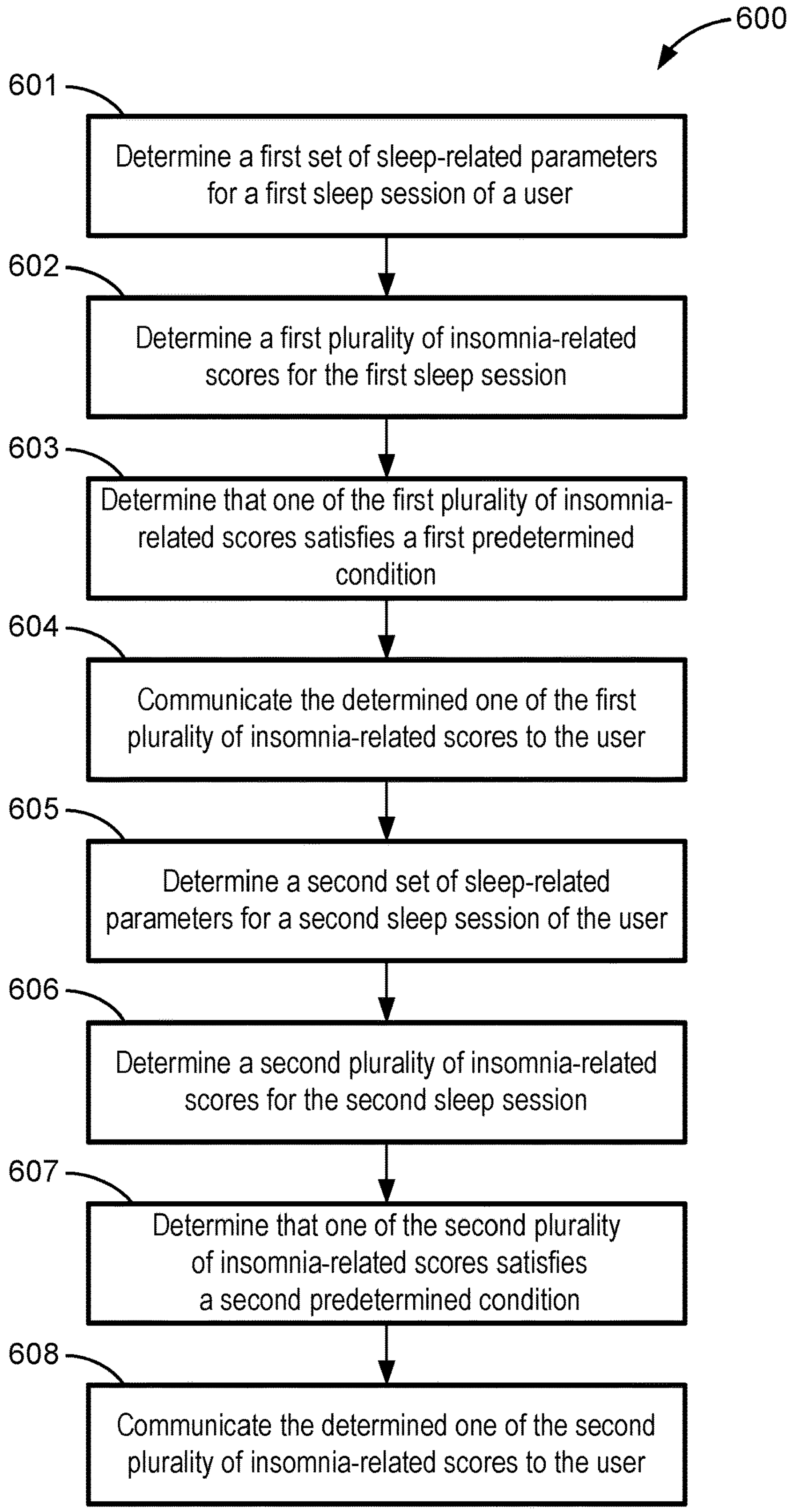
FIG. 6 is a process flow diagram for a method of communicating one or more insomnia-related scores to a user, according to some implementations of the present disclosure.

Referring to FIG. 6, a method 600 according to some implementations of the present disclosure is illustrated. The method 600 can be implemented using any combination of elements or aspects of the system 100 described herein.

Step 601 of the method 600 is the same as, or similar to, step 502 of the method 500 (FIG. 5) and includes determining a first set of sleep-related parameters for a first sleep session of a user. The first step of sleep-related parameter can be determined based at least in part on first physiological data associated with the user that is generated (e.g., by at least one of the one or more sensors 130) and received (e.g., by the electronic interface 119) during the first sleep session.

Step 602 of the method 600 is the same as, or similar to, step 504 of the method (500) and includes determining a first plurality of insomnia-related scores for the first sleep session based at least in part on the first set of sleep-related parameters (step 601) and/or a user profile associated with the user that is the same as, or similar to, the user profile(s) described herein. Each of the first plurality of insomnia-related score is associated with at least a corresponding one of the first set of sleep-related parameters (step 601).

Step 603 of the method 600 includes determining that a first insomnia-related score of the first plurality insomnia-related scores (step 602) satisfies a first predetermined condition. As described herein for step 604, information indicative of the first insomnia-related score that is determined or identified during step 603 is communicated to the user subsequent to the first sleep session. In some examples, it is advantageous to identify the highest or "best" one of the first plurality of insomnia-related scores and communicate that score to the user to provide positive feedback and reinforcement. That is, the first insomnia-related score is selected to aid in causing the user to perceive that they experienced quality or effective sleep during the first sleep session (e.g., to reduce or prevent paradoxical insomnia).

Thus, in some implementations, the first predetermined condition can be that the first insomnia-related score has a highest value relative to the other ones of the first plurality of insomnia-related scores (e.g., where the score is scaled between 1-10 with 10 being indicative of the best score and 1 being indicative of the worst score). Alternatively, first predetermined condition can be that the first insomnia-related score has a lowest value relative to the other ones of the first plurality of insomnia-related scores (e.g., where the score is scaled between 1-10 with 1 being indicative of the best score and 10 being indicative of the worst score).

Step 604 of the method 600 includes causing an indicator of the first insomnia-related score (step 603) to be communicated to the user in the same or similar manner as described above for step 506 of the method 500 (FIG. 5). For example, the indicator of the first insomnia-related score can be communicated to the user via the display 172 of the user device 170 (FIG. 1) described herein.

In some implementations, the method 600 includes determining a first recommendation associated with the first insomnia-related score (step 603). The first recommendation can be determined to aid the user in improving or maintaining the first insomnia-related score for a next sleep session. The first recommendation can be determined in the same or similar manner as described above for the recommendations determined during the method 500 (FIG. 5), such as, for example, determining the first recommendation based at least in part on the user profile.

In some implementations, the method 600 includes updating the user profile subsequent to the first sleep session to include the first set of sleep-related parameters for the first sleep session (step 601), the plurality of insomnia-related scores (step 602), the first insomnia-related score (step 603), or any combination thereof.

Step 605 of the method 600 is similar to step 601 and includes determining a second set of sleep-related parameters for a second sleep session of the user. The second set of sleep-related parameter can be determined based at least in part on second physiological data associated with the user that is generated (e.g., by at least one of the one or more sensors 130) and received (e.g., by the electronic interface 119) during the second sleep session.

Step 606 of the method 600 is similar to step 602 and includes determining a second plurality of insomnia-related scores for the second sleep session based at least in part on the second set of sleep-related parameters (step 605) and/or the user profile. Each of the second plurality of insomnia-related score is associated with at least a corresponding one of the second set of sleep-related parameters (step 605).

Step 607 of the method 600 includes determining that a second insomnia-related score of the second plurality insomnia-related scores (step 606) satisfies a second predetermined condition. The sleep-related parameter associated with the determined second score (step 607) can be the same as, or different than, the sleep-related parameter associated with the first score (step 603). Similarly, the second predetermined condition (step 607) can be the same as, or different than, the first predetermined condition (step 603).

When comparing the first plurality of insomnia-related scores for the first sleep session (step 603) and the second plurality of insomnia-related scores for the second sleep session (step 606), some or all of the scores may improve or decline in the second sleep session relative to the first sleep session. Thus, for example, it may be advantageous to determine which of the second plurality of insomnia-related sleep scores for the second sleep session improved the most relative to the corresponding score in the first plurality of insomnia-related scores for the first sleep session. In another example, in cases where some of the insomnia-related scores decreased for the second sleep session, it can be advantageous to identify an insomnia-related score that increased or improved relative to the corresponding score from the first sleep session and communicate that score to the user. Thus, in some implementations, the second predetermined condition can be selected to identify the second insomnia-related score as having improved the most relative to the one of the first plurality of insomnia-related scores from the first sleep session (e.g., which may not be the same as the first insomnia-related score determined during step 603). Similarly, in some examples, the second predetermined condition can be selected to identify the second insomnia-related score as having decreased or declined the least relative to the one of the first plurality of insomnia-related scores from the first sleep session (e.g., which may not be the same as the first insomnia-related score determined during step 603).

While step 603 and step 607 have been described herein as determining or identifying one insomnia-related score based on a predetermined condition, in some implementations, a plurality of insomnia-related scores can be determined or identifying during step 603 and/or step 607 based on one or more predetermined conditions. For example, in some implementations, step 603 can include determining a first insomnia-related score and a second insomnia-related score for the first sleep session based at least in part on a first predetermined condition or a first plurality of predetermined conditions, and step 607 can include determining a third insomnia-related score and a fourth insomnia-related score for the second sleep session based at least in part on a second predetermined condition or a second plurality of predetermined conditions.

Step 608 of the method 600 includes communicating the determined second insomnia-related score (step 607) to the user in the same or similar manner as the first insomnia-related score (step 604). One or more of the steps of the method 600 described herein can be repeated one or more time for additional sleep sessions (e.g., a third sleep session, a fourth sleep session, a tenth sleep session, etc.).

One or more elements or aspects or steps, or any portion(s) thereof, from one or more of any of claims below can be combined with one or more elements or aspects or steps, or any portion(s) thereof, from one or more of any of the other claims or combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A system comprising:

an electronic interface configured to receive (i) first physiological data associated with a user during a first sleep session, the first physiological data being generated by a first sensor, (ii) second data associated with the user subsequent to the first sleep session and prior to a second sleep session, and (iii) third physiological data associated with the user during the second sleep session;

a memory storing machine-readable instructions; and a control system including one or more processors configured to execute the machine-readable instructions to:

determine a first set of sleep-related parameters for the first sleep session based at least in part on the first physiological data, the first set of sleep-related parameters including a sleep onset latency, a number of awakenings, a frequency of awakenings, or any combination thereof;

determine a first plurality of insomnia-related scores for the first sleep session, each one of the first plurality of insomnia-related scores being associated with a corresponding one of the first set of sleep-related parameters, and each one of the first plurality of insomnia-related scores being standardized based on previously recorded sleep-related parameters for the user, previously recorded sleep-related parameters for a plurality of other users, or any combination thereof;

identify a first one of the first set of sleep-related parameters as a first targeted parameter based at least in part on a user profile associated with the user, wherein the first targeted parameter is one of the first set of sleep-related parameters that is predicted to reduce one or more insomnia-related symptoms for the user during the second sleep session;

cause first information indicative of (i) the first targeted parameter, (ii) a first recommendation associated with the first targeted parameter, or both (i) and (ii) to be communicated to the user via a user device;

update the user profile to include at least a portion of the determined first set of sleep-related parameters and at least a portion of the second data;

determine a second set of sleep-related parameters for the second sleep session based at least in part on the third physiological data, the second set of sleep-related parameters including a second sleep onset latency, a second number of awakenings, a second frequency of awakenings, or any combination thereof;

identify a second one of the second set of sleep-related parameters as a second targeted parameter based at least in part on the updated user profile; and cause second information indicative of (i) the second targeted parameter, (ii) a second recommendation associated with the second targeted parameter, or both (i) and (ii) to be communicated to the user via the user device.

2. The system of claim 1, wherein the user profile includes demographic information associated with the user, biometric information associated with the user, medical information associated with the user, previously-recorded sleep parameters associated with the user, or any combination thereof.

3. The system of claim 2, wherein the second data includes user feedback provided by the user via the user device subsequent to the control system causing the first information to be communicated to the user.

4. The system of claim 3, wherein the user feedback includes an indication of user diet, an indication of user stress, an indication of user anxiety, an indication of user inhibitors, an indication of user television usage, an indication of user caffeine usage, an indication of user drug usage, an indication of user alcohol usage, an indication of user nicotine usage, an indication of user marijuana usage, an indication of user mediations, an indication of user mental illnesses, an indication of user perceived sleep quality, an indication of user perceived total sleep time, an indication of user perceived sleep onset time, an indication of physical activity of the user, an indication of user subjective sleepiness, an indication of user subjective fatigue, or any combination thereof.

5. The system of claim 4, wherein the first recommendation is determined based at least in part on the user profile.

6. The system of claim 1, wherein the second targeted parameter is one of the second set of sleep-related parameters that is predicted to further reduce one or more insomnia-related symptoms for the user during a third sleep session that is subsequent to the second sleep session.

7. The system of claim 1, wherein the control system is further configured to determine a first plurality of insomnia-related scores, each of the first plurality of insomnia-related scores being associated with a corresponding one of the first set of sleep-related parameters.

8. The system of claim 7, wherein the first information indicative of the first targeted parameter includes a first one of the first plurality of insomnia-related scores that is associated with the first targeted parameter.

9. The system of claim 1, wherein the first set of sleep-related parameters further includes a total light sleep time for the first sleep session, a total deep sleep time for the first sleep session, a total REM sleep time for the first sleep session, a total sleep time for the first sleep session, a respiration signal during at least a portion of the first sleep session, a respiration rate during at least a portion of the first sleep session, an inspiration amplitude during at least a portion of the first sleep session, an expiration amplitude during at least a portion of the first sleep session, an inspiration-expiration ratio during at least a portion of the first sleep session, one or more events during at least a portion of the first sleep session, a number of events per hour during at least a portion of the first sleep session, a pattern of events during at least a portion of the first sleep session, a sleep state during at least a portion of the first sleep session, or any combination thereof.

10. The system of claim 1, wherein the control system is further configured to update the user profile subsequent to the first sleep session and prior to the second sleep session.

11. The system of claim 1, wherein the control system is further configured to cause the first information to be communicated to the user via the user device subsequent to the first sleep session and prior to the second sleep session.

12. The system of claim 1, wherein the first set of sleep-related parameters, the second set of sleep-related parameters, or both further include a wake-after-sleep-onset parameter, a sleep efficiency, a sleep fragmentation index, or any combination thereof.

13. A system comprising:

an electronic interface configured to receive (i) first physiological data associated with a user during a first sleep session and (ii) second physiological data associated with the user during a second sleep session, the first physiological data and the second physiological data being generated by one or more sensors;

a memory storing machine-readable instructions; and a control system including one or more processors configured to execute the machine-readable instructions to:

determine a first set of sleep-related parameters, wherein the first set of sleep-related parameters is determined for the first sleep session based at least in part on the first physiological data, the first set of sleep-related parameters including a first sleep onset latency, a first number of awakenings, a first frequency of awakenings, or any combination thereof;

determine a first plurality of insomnia-related scores for the first sleep session, each one of the first plurality of insomnia-related scores being associated with a corresponding one of the first set of sleep-related parameters, and each one of the first plurality of insomnia-related scores being standardized based on previously recorded sleep-related parameters for the user, previously recorded sleep-related parameters for a plurality of other users, or any combination thereof;

determine that a first one of the first plurality of insomnia-related scores satisfies a first predetermined condition;

cause a first indication to be communicated to the user via a user device, the first indication being of (i) the first one of the first plurality of insomnia-related scores, (ii) the first one of the first set of sleep-related parameters, or (iii) both (i) and (ii);

determine a second set of sleep-related parameters, wherein the second set of sleep-related parameters is determined for the second sleep session based at least in part on the second physiological data, the second set of sleep-related parameters including a second sleep onset latency, a second number of awakenings, a second frequency of awakenings, or any combination thereof;

determine a second plurality of insomnia-related scores for the second sleep session, each one of the second plurality of insomnia-related scores being associated with a corresponding one of the second set of sleep-related parameters, and each one of the first plurality of insomnia-related scores being standardized based on previously recorded sleep-related parameters for the user, previously recorded sleep-related parameters for a plurality of other users, or any combination thereof;

determine that a second one of the second plurality of insomnia-related scores satisfies a second predetermined condition; and cause a second indication to be communicated to the user via the user device, the second indication being of (i) the second one of the second plurality of insomnia-related scores, (ii) the second one of the second set of sleep-related parameter, or (iii) both (i) and (ii).

14. The system of claim 13, wherein the control system is further configured to update a user profile associated with the user based at least in part on the determined first plurality of insomnia-related scores, the determined second plurality of insomnia-related scores, or both.

15. The system of claim 13, wherein the first predetermined condition is that the first insomnia-related score of the first plurality of insomnia-related scores has a highest value relative to the other ones of the first plurality of insomnia-related scores and the second predetermined condition is that the second insomnia-related score for the second sleep session is higher than the first insomnia-related score for the first sleep session.

16. The system of claim 13, wherein the first predetermined condition is that the first insomnia-related score of the first plurality of insomnia-related scores has a lowest value relative to the other ones of the first plurality of insomnia-related scores and the second predetermined condition is that the second insomnia-related score for the second sleep session is lower than the first insomnia-related score for the first sleep session.

17. The system of claim 13, wherein each of the first plurality of insomnia-related scores is a numerical value scaled between a lower limit and an upper limit.

18. The system of claim 17, wherein the lower limit is 0 and the upper limit is 10.

19. The system of claim 13, wherein the control system is further configured to execute the machine-readable instructions to determine a first recommendation for the user based at least in part on the first insomnia-related score, one or more of the first plurality of sleep-related parameters, or both; and cause an indication of the first recommendation to be communicated to the user subsequent to the first sleep session and prior to the second sleep session.

20. The system of claim 19, wherein the second predetermined condition is (i) that the second one of the second set of sleep-related parameters associated with the second insomnia-related score is the same as the first one of the first set of sleep-related parameters associated with the first insomnia-related score and the second insomnia-related score for the second sleep session is greater than the first insomnia-related score for the first sleep session or (ii) wherein the second predetermined condition is that the second sleep-related parameter associated with the second insomnia-related score is different than the first sleep-related parameter associated with the first insomnia-related score and the second insomnia-related score for the second sleep session is greater than the first insomnia-related score for the first sleep session.

21. The system of claim 19, wherein the electronic interface is configured to receive information indicative of user feedback from the user subsequent to the first sleep session and prior to the second sleep session, wherein the user feedback includes an indication of user diet, user stress, an indication of user anxiety, an indication of user inhibitors, an indication of user television usage, an indication of user caffeine usage, an indication of user drug usage, an indication of user alcohol usage, an indication of user nicotine usage, an indication of user marijuana usage, an indication of user mediations, an indication of user mental illnesses, an indication of user perceived sleep quality, an indication of user perceived sleep time, an indication of physical activity of the user, an indication of user subjective sleepiness, an indication of user subjective fatigue, a user reaction to the first indication, or any combination thereof.

22. The system of claim 21, wherein the control system is further configured to execute the machine-readable instructions to determine the first recommendation based at least in part on the user feedback from the user, wherein the first recommendation includes a recommended bedtime for the second sleep session, a recommended wake-up time for the second sleep session, a recommended sleep duration for the second sleep session, a recommended diet, a recommended activity, a recommended medication use, or any combination thereof.

23. The system of claim 13, wherein the first set of sleep-related parameters and the second set of sleep-related parameters further include sleep a light sleep time, a deep sleep time, a REM sleep time, a total sleep time, a respiration signal, a respiration rate, an inspiration amplitude, an expiration amplitude, an inspiration-expiration ratio, one or more events, a number of events per hour, a pattern of events, a sleep state, or any combination thereof.

24. A method comprising:

receiving first physiological data associated with a user for a first sleep session;

determining a first set of sleep-related parameters based at least in part on the first physiological data, the first set of sleep-related parameters including a first sleep onset latency, a first number of awakenings, a first frequency of awakenings, or any combination thereof;

determining a first plurality of insomnia-related scores for the first sleep session, each one of the first plurality of insomnia-related scores being associated with a corresponding one of the first set of sleep-related parameters, and each one of the first plurality of insomnia-related scores being standardized based on previously recorded sleep-related parameters for the user, previously recorded sleep-related parameters for a plurality of other users, or any combination thereof;

identifying a first one of the first plurality of insomnia-related scores that satisfies a first predetermined condition;

causing a first indication to be communicated to the user via a user device, the first indication being of (i) the first one of the first plurality of insomnia-related scores, (ii) the first one of the first set of sleep-related parameters, or (iii) both (i) and (ii);

receiving second physiological data associated with a user for a second sleep session, wherein the second sleep session is subsequent to the first sleep session;

determining a second set of sleep-related parameters, wherein the second set of sleep-related parameters is determined for the second sleep session based at least in part on the second physiological data, the second set of sleep-related parameters including a second sleep onset latency, a second number of awakenings, a second frequency of awakenings, or any combination thereof;

determining a second plurality of insomnia-related scores, wherein the second plurality of insomnia-related scores is determined for the second sleep session, each one of the second plurality of insomnia-related scores being associated with a corresponding one of the second set of sleep-related parameters;

identifying a second one of the second plurality of insomnia-related scores that satisfies a second predetermined condition; and causing a second indication to be communicated to the user via the user device, the second indication being of (i) the second one of the second plurality of insomnia-related scores, (ii) the second one of the second set of sleep-related parameters, or (iii) both (i) and (ii).

* * * * *